United States Patent [19]
Andrus et al.

[11] Patent Number: 5,888,172
[45] Date of Patent: Mar. 30, 1999

[54] PHYSICAL EXERCISE VIDEO SYSTEM

[75] Inventors: Bryan DeWitt Andrus, Riverwoods, Ill.; Martin Sikes, Vancouver, Canada; Christopher David Glen Robertson, Vancouver, Canada; Roderick Armes, Vancouver, Canada; Mark Joseph Slemko, Vancouver, Canada; Andrew G. Maduza, Aurora; Augustine Nieto, Winnetka, both of Ill.

[73] Assignee: Brunswick Corporation, Lake Forest, Ill.

[21] Appl. No.: 886,334

[22] Filed: Jul. 1, 1997

Related U.S. Application Data

[60] Continuation of Ser. No. 682,285, Jul. 17, 1996, abandoned, which is a division of Ser. No. 75,589, filed as PCT/US93/00724, Jan. 27, 1993, Pat. No. 5,591,104.

[51] Int. Cl.[6] ..................................................... A63B 21/00
[52] U.S. Cl. ........................ 482/7; 482/1; 482/3; 482/4; 482/5; 482/901; 482/902; 434/247; 434/257
[58] Field of Search ........................ 482/1–9, 51, 57–66, 482/901–903; 434/247, 257; 601/23, 33

[56] References Cited

U.S. PATENT DOCUMENTS 5,213,555  5/1993  Hood et al. ................................ 482/57
5,308,296  5/1994  Eckstein ...................................... 482/5
5,527,239  6/1996  Abbondanza ............................... 482/8

*Primary Examiner*—Glenn E. Richman
*Attorney, Agent, or Firm*—Michael B. McMurry

[57] ABSTRACT

A physical exercise video system includes a physical exercise machine (22), a video system (24) and an interface module (26). The video system (24) has a computer (28) and a removable cartridge (34). The interface module (26) is interposed between the computer (28) and cartridge (34), and provides interactive communications between the computer (28) and exercise machine (22). A communication protocol governs this communication, and includes specifications for status and command data packets. The video system (24) and exercise machine (22) can be selectively operated as either stand-alone units, or in an interactive exercise mode, wherein the exercise data by the exercise machine (22) affects the output of the video system (24), and may also be stored in memory within the interface module (26). The video system (24) controls the operation of the exercise machine (22) generally, and specifically, controls the load resistance imposed in opposition to the movement of pedals (66). The control of load resistance by video system (24) is a function of the operating characteristics of the exercise machine (22).

10 Claims, 11 Drawing Sheets

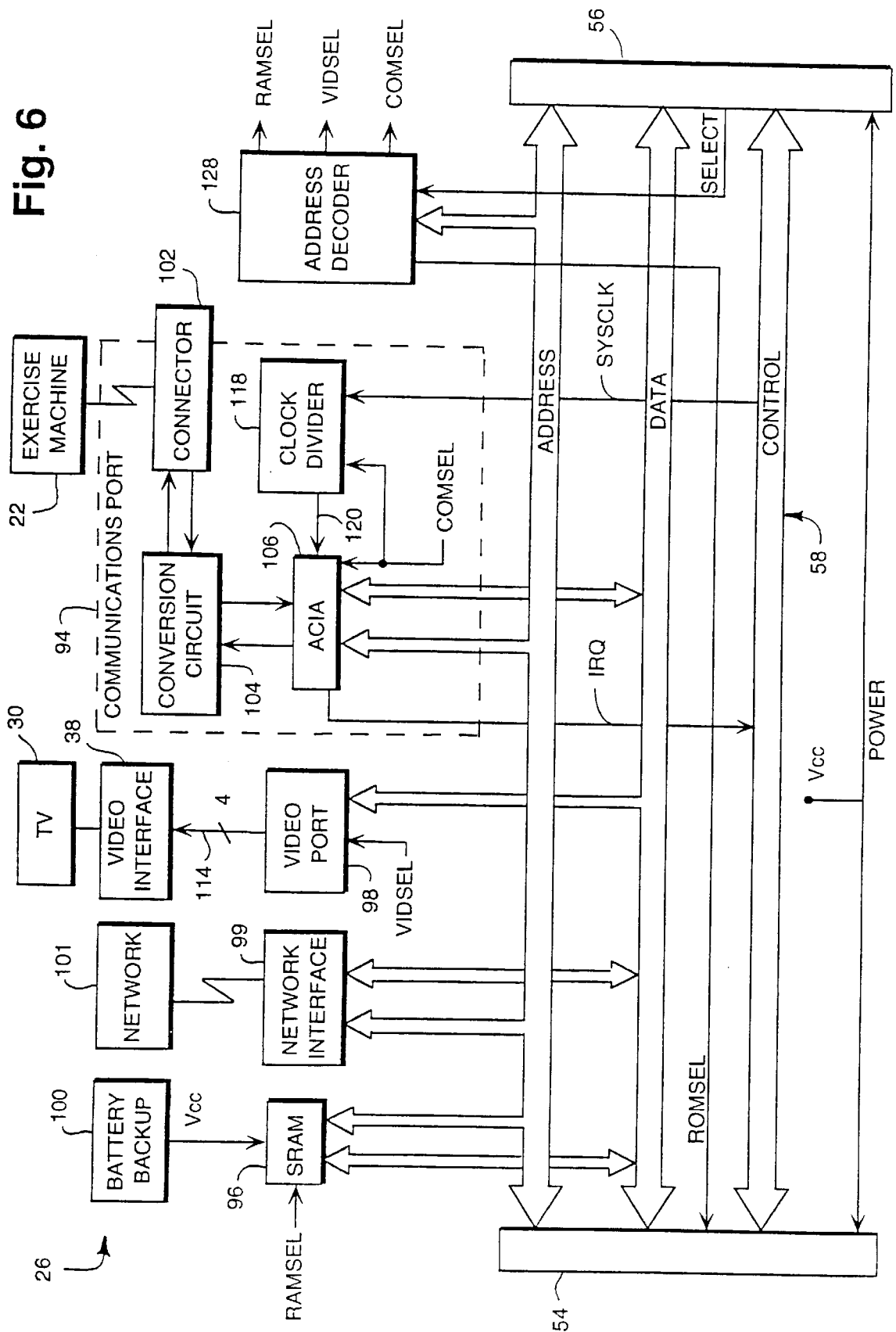

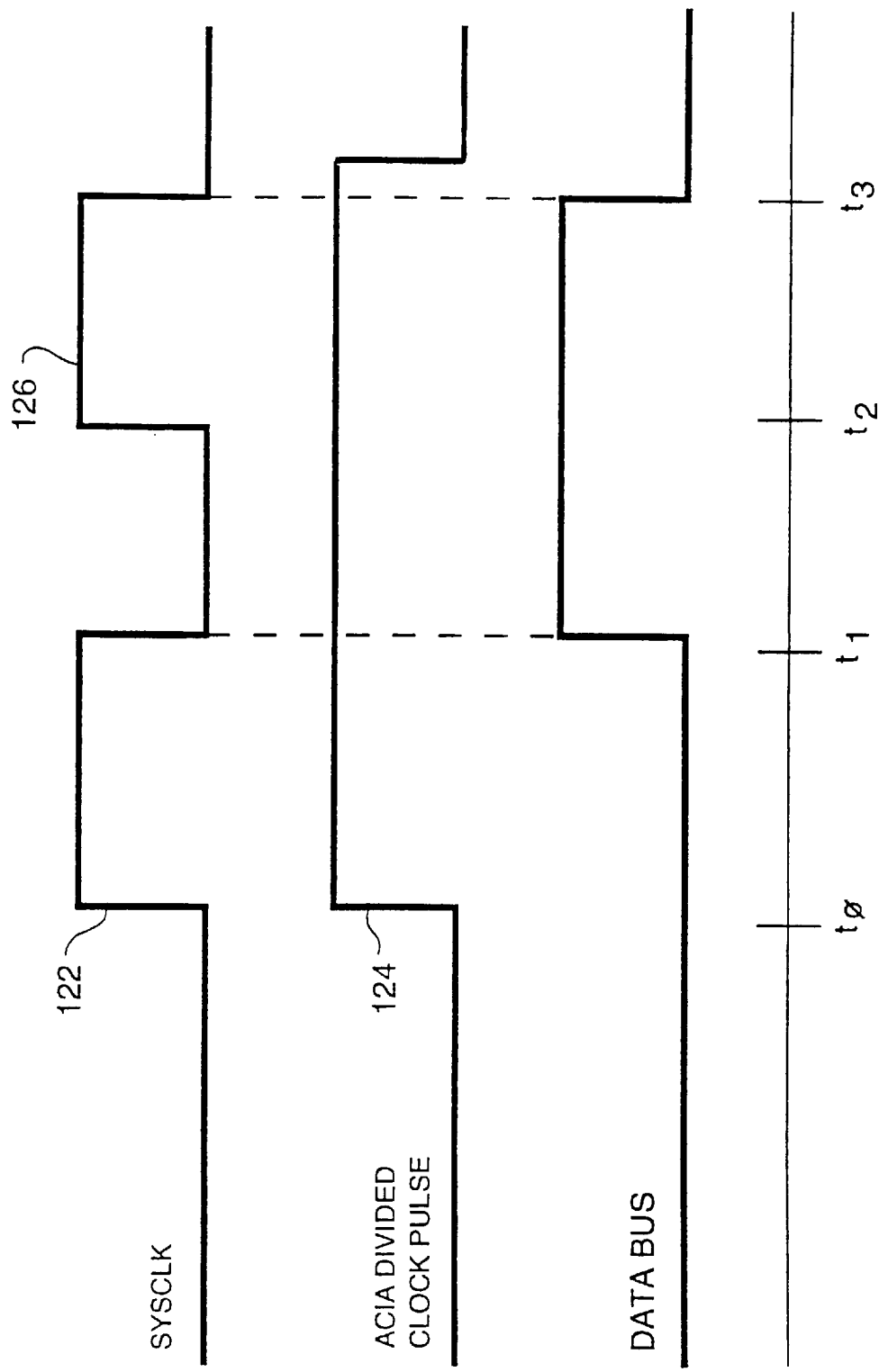

| $D_0$ | STATUS BYTE |
|---|---|
| $D_1$ | RPM |
| $D_2$ | ELAPSED MINUTES |
| $D_3$ | ELAPSED SECONDS |
| $D_4$ | USER-SELECTED LEVEL |
| $D_5$ | MACHINE TYPE |

| $D_0$ | COMMAND |
|---|---|
| $D_1$ | LOAD VALUE |
| $D_2$ | DISPLAY |
| $D_3$ | DISPLAY |
| $D_4$ | DISPLAY |
| $D_5$ | DISPLAY |

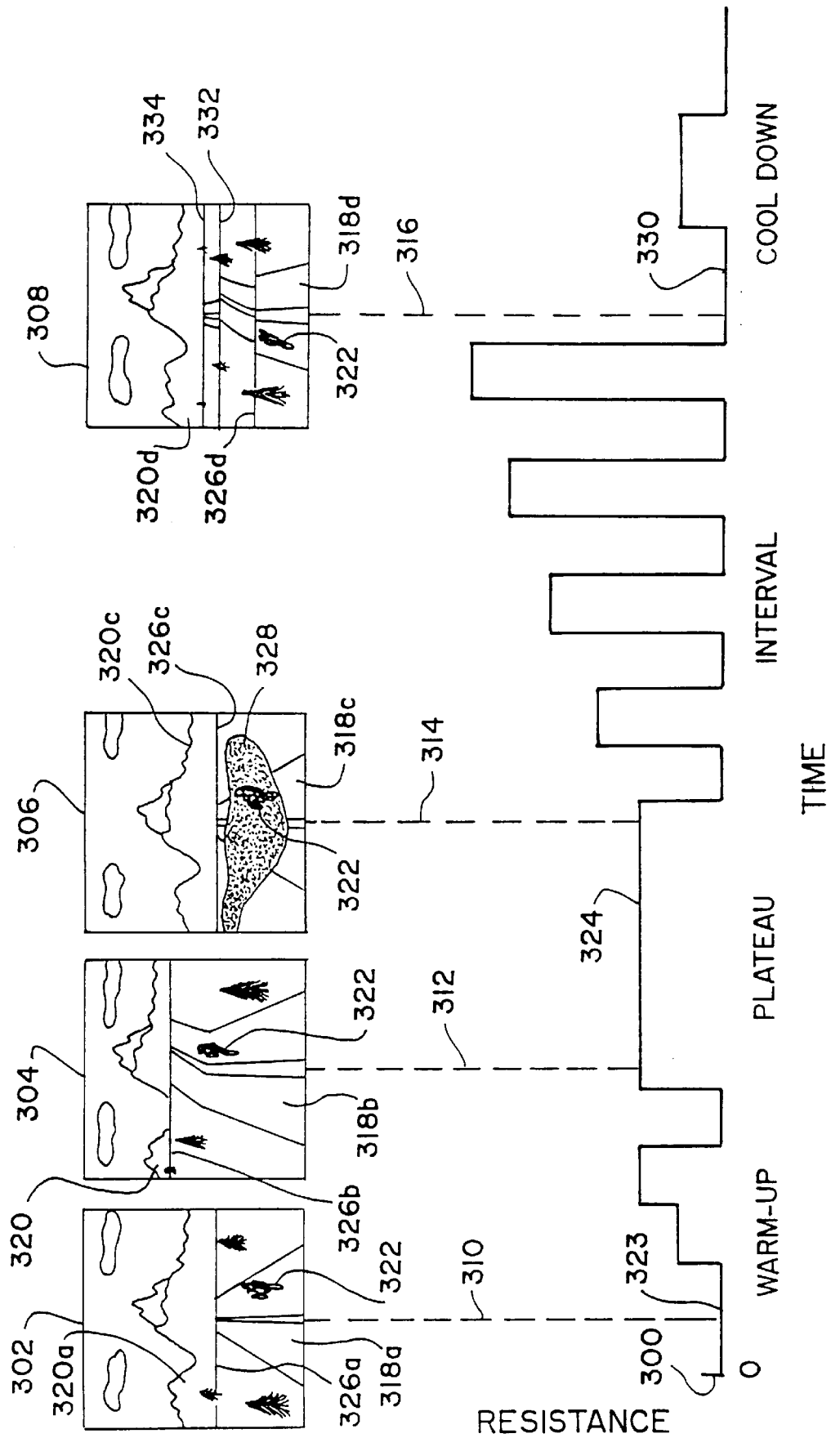

PHYSICAL EXERCISE VIDEO SYSTEM

This application is a continuation of Ser. No. 08/682,285 Filed Jul. 17, 1996, now abandoned, which is a divisional of Ser. No. 08/075,589, filed as PCT/US93/00724, Jan. 27, 1993, now U.S. Pat. No. 5,591,104.

TECHNICAL FIELD

This invention relates to physical exercise video systems, and in particular to interactive video systems which are adapted for use with physical exercise machines.

BACKGROUND ART

For years, people have recognized the health benefits of aerobic exercise. As a result, many stationary exercise devices have been introduced, including bicycles, treadmills, rowing machines and stair climbers, to name but a few. These devices typically engage users in repetitive exercise motions, such as pedaling, stepping, pulling or running. This exercise movement is resisted (often variably) to induce physical exertion, leading to aerobic exercise.

Despite the many benefits of exercise, some users find it tedious or boring, and this has discouraged many from regular exercise. Coincidentally, while some people shunned exercise, a large number (particularly teenagers) became television and video game enthusiasts. This development did not go unnoticed by the exercise equipment industry, which over the years has attempted to make exercise more interesting by associating it with some form of visual entertainment, particularly television or video games. And although there have been many attempts to meld exercise and video, none of these efforts have yielded completely satisfactory results.

By way of background, many commercially available video systems, such as those sold under the trademarks Nintendo, sega and Atari, are computer-based interactive video game systems which display game output on a conventional television. Game control peripherals (often referred to as "joysticks") are interfaced to the game system through plug-in ports or jacks to provide user interaction with the action depicted on the screen. Typically, removable memory cartridges containing various programs allow the game system to execute different games or other interactive programs. While these cartridge-type game systems are of great interest, interactive video programs, including games, can be played on other types of video systems, such as, for example, personal computers. Moreover, video systems encompass an array of technologies including interactive video games, educational programs, broadcast and cable television and prerecorded video systems such as VCRs.

There have been attempts to interface exercise machines with interactive video systems by treating the exercise machine as simply another type of game control peripheral or joystick. Some examples of these efforts include U.S. Pat. No. 4,817,950 (player moves figure of surfer on video screen by moving simulated surfboard with player's feet); U.S. Pat. No. 4,711,477 (movement of pedals, handles and swivel seat by player control aim of video-displayed gun); U.S. Pat. No. 5,054,771 (movement of swingable member and swivel seat controls position of marker on a screen); U.S. Pat. No. 4,512,567 (movement of handlebars and pedal rpm enable stationary bicycle to control video game); and U.S. Pat. No. 5,139,261 (adjustable pressure sensors placed on floor generate video game input when pressed by a user).

Other, more sophisticated, efforts have used a video game or like apparatus to control the load resistance experienced by the user. Some examples of these efforts include U.S. Pat. No. 5,001,632 (speed or skill level of opponent in video game increases when heart rate falls outside of predetermined range); U.S. Pat. No. 4,709,917 (computer adjusts load resistance of bicycle in accordance with type of terrain depicted in video display of road); and U.S. Pat. No. 5,029,846 (load resistance varied in accordance with simulated hill profile depicted on spinning reel).

None of these attempts have resulted in a practicable and widely accepted combination of exercise equipment and video systems. One reason is that these past efforts tended to focus narrowly on specific game control hardware (such as swivel seats or simulated surfboards). In other cases, these approaches address only the specific manner in which a video game system might respond to exercise conditions (for example, scenery passes by more quickly with increased pedal rpm, or opponents become more powerful when heart rate is too low). These limitations are unacceptable to both users and game developers. On the one hand, users demand hardware that will execute a wide variety of games and programs. On the other hand, developers can only afford to invest in programs that will execute on a large number of systems.

DISCLOSURE OF INVENTION

In accordance with the invention a flexible and powerful interface is provided that will result in substantially improved communication between exercise machines and video systems such as video games. As discussed above, other combinations of video games with exercise equipment tend to be isolated, specific implementations of exercise equipment adapted for video game interface. In contrast, the present invention provides interfaces including hardware configurations, software techniques and communications protocols, which allow a wide variety of exercise equipment to interface with video systems, including television and interactive video games.

1. Interface Module.

One object of the invention is to provide an exercise video system having an exercise machine, a video system and an interface module for enabling two-way communication therebetween. The video system is preferably a cartridge-type video game system which uses a conventional television as a display. However, other video systems can be used.

In one embodiment, the exercise machine includes an exercise structure, which can be a stationary bicycle, treadmill, rowing machine, skier, stair climber or other such device, for example. The exercise structure is characterized by its ability to provide the user with an exercise movement, such as pedaling, rowing or stepping, for example. A load device, such as an alternator, applies a load resistance in opposition to the exercise movement to induce aerobic exercise. The load device varies the level of load resistance in accordance with a load control signal. The exercise machine also includes at least one sensor which generates as output an exercise condition signal which can, for example, represent one or more of the following: heart rate, pedal rpm, calorie consumption, or other exercise-related data.

In accordance with the invention, the interface module is interposed between the video system's control unit and memory cartridge to provide a parallel bus connection therebetween. Included within the interface module and coupled to the bus connection is a communications port. The communications port is linked to the exercise machine, which is also equipped with a suitable communications interface for providing two-way communication between the exercise machine and the interface module.

In accordance with the invention, the exercise machine transmits the exercise condition signal to the video system through the interface module, enabling the user to operate an interactive video game or other program in which the user's exercise performance affects game outcome. Moreover, the video system can transmit a load control signal to the exercise machine so as to vary load resistance in accordance with the outcome of the video game. In this manner, the user receives not only visual feedback via the television or other display, but also receives feedback in the form of changing load resistance.

2. Communications Protocol.

Another object of the invention is to provide a protocol for establishing communication between an exercise machine and a video system. The protocol can be practiced with the hardware configuration described above, or other suitable variations.

Under the protocol, the exercise machine and video system are connected for two-way communication by, for example, the above-described interface module. The exercise machine periodically sends out a status data packet. When the video system receives this status data packet, it responds with a command data packet.

The status data packet includes data bytes indicating the status of the exercise machine, certain predetermined exercise conditions such as, for example, heart rate, pedal rpm, calorie consumption and the type of the exercise machine. The command data packet includes a command data byte which includes initialize and update commands, for example. The command data packet also contains data bytes, which, in the case of the update command, are used to update or adjust operation of the exercise machine. Typically, these adjustments involve varying the load resistance and updating the control panel display.

In accordance with the invention, the exercise machine can also send a special status data packet which includes a specification describing the operating characteristics of the exercise machine. Alternatively, the special status data packet can include a code associated with the particular exercise device. In this case, a table is maintained in memory of the video system for storing the operating characteristics of the exercise machine associated with each code.

3. Multi-Modal Operation.

It is yet another object of the invention to provide a combination exercise machine and video system which operates in several different modes, including interactive exercise mode, graphic overlay mode and stand-alone (or "game") mode. In the interactive exercise and graphic overlay modes, the exercise machine and video system are in two-way communication. In the case of the interactive exercise mode, the video system generates a video output (such as a game display), while the user interacts with the video system via the exercise machine and/or conventional game control peripherals. In the case of the graphic overlay mode, the video system overlays exercise data onto an external CATV or other video signal. Contrastingly, in stand-alone mode, the video system and exercise machine operate independently.

In accordance with the invention, the user can select the desired mode of operation. Additional modes are possible. In multi-player video games, it is also possible for the first player to operate the game using an exercise machine in interactive exercise mode, while a second player also operates the game using conventional game controls in a stand-alone mode. In this mode two players, only one of whom is using the exercise machine, can compete with each other in the same video game. Similarly, it is possible to have two exercise machines connected to the video system so that the players can compete in a video game using the exercise machine.

4. Dynamic Control of Exercise Machine.

Still another object of the invention is to provide a video system which controls the load resistance or other operating characteristic of an exercise machine in a manner which is well-coordinated with the video system's visual display or other program result.

In accordance with the invention, the video system and exercise machine are adapted for two-way communication. The exercise machine includes a load device for applying a variable level of load resistance in response to a load control signal. The video system generates a program result (such as an animated display), and controls the exercise machine's load resistance as a function of both the program result and the operating characteristics of the exercise machine, including load response. In this manner, changes in actual imposed load occur concurrently with changes in video display or other program results.

In one embodiment, the video system is a cartridge-type video game system. The game system is interfaced with an exercise machine so that the user's exercise performance affects game play, and the game play affects the load resistance imposed on the user by the exercise machine. The game includes an animated display of a race over terrain of varying grade and quality. The video system's computer adjusts the load resistance of the exercise machine in accordance with both the variations in the depicted terrain and the exercise machine's load response. By taking load response into account, the changes in load resistance more realistically correspond to the program results.

For example, if the exercise machine uses an alternator having a nearly instantaneous response to changes in the load control signal, the video system will vary the load control signal simultaneously with variations in the depicted terrain. However, if the exercise machine uses a band or eddy current brake having a delayed response to changes in the load control signal, then the video system will change the load control signal prior to the displayed variations in the terrain. In this manner, the user does not experience discontinuity between the depiction of terrain variations and the imposition of load resistance.

In one embodiment, the exercise machine communicates its operating characteristics to the video system. This can be accomplished in accordance with the above-described or other communications protocols. Alternatively, the video system can transmit desired current and future load values to the exercise machine. The exercise machine can then adjust the load control signal to achieve the desired future load resistances in accordance with its particular operating characteristics.

5. Graphic Overlay Mode.

An additional object of the invention is to provide an exercise machine adapted for interface with a video system, and having the capability of displaying exercise data on a video monitor, such as a television, that is adapted for receiving and displaying an external video signal such as a CATV or television broadcast. In accordance with the invention, exercise data is superimposed over the external signal. It is also possible for the user to switch back and forth between watching television and playing an interactive video game or other program.

One embodiment of the invention includes an exercise machine, a cartridge-type video game system, a communications interface, a video interface and a television. The video interface is interposed between the external video signal and the television, and includes an overlay circuit that superimposes data onto the external video signal. The video interface is linked via wire or radio frequency signal to a video port located within the communication interface. The video port is coupled to the video system so that the video system can write exercise data to the video port for superimposition on the external video signal by the video overlay circuit. Alternatively, the video port may be coupled directly to the exercise machine.

In one embodiment, the video interface includes a switch. The switch has a first input connected to the video signal output of the video system, and a second input adapted for receiving an external video signal from a CATV tuner or VCR, for example. The switch includes an output that is coupled to the video overlay circuit, and is adapted for selectively coupling the external video signal and video system output to the overlay circuit. By operating the switch, the user can display either the external video signal or the video system output on the television.

In accordance with one aspect of the invention, the switch is responsive to a control signal which is generated by the video system. In cases where the video system can operate in both the interactive exercise mode and the graphic overlay mode, the switch allows the video system to toggle between the two modes in response to a user's command. For example, a user playing a video game in the interactive exercise mode can switch to the graphic overlay mode. Here the video system will suspend execution of the game program, operate the switch to display a CATV or other external video signal on the television, and then commence operation in the graphic overlay mode, described above.

6. Storage of Exercise Data.

Yet another object of the invention is to provide a method for storing exercise information in a combination exercise machine and video system. In accordance with the invention, the combination includes an interface module for enabling communication between the exercise machine and a cartridge-type video system. The interface module includes a nonvolatile random access memory which is addressable by the video system for storing exercise data.

In one embodiment, the interface module is interposed between the cartridge and the video system's control unit. The interface module includes a communications port which enables two-way communication between the video system and the exercise machine. The interface module also includes memory which is addressable by the video system.

During exercise, the exercise machine transmits exercise data to the video system via the interface module. The video system periodically writes this information to the memory. In this manner, the user can maintain a record of exercise data, even if the cartridge or, for that matter, the video system is replaced. This is particularly useful where the user from time to time exercises with a cartridge-resident exercise training program. The exercise training program can access the exercise data stored in the interface module, even though that data may have been generated while the user was exercising with a different training program or even a video game.

In some cases, game cartridges include a standard routine for recording in memory exercise data in accordance with a predetermined format. In this manner, exercise training programs can include routines which recognize and use data stored in the predetermined format by the video games and other programs.

7. Remote Control of Exercise Machine.

A further object of the invention is to provide a combination computer-controlled exercise machine and computerized video system, wherein the computer processing and display power of the video system are used to remotely handle the computer-controlled operational and display features of the exercise machine.

In accordance with the invention, the apparatus includes an exercise machine, a video system that is remote from the exercise machine, and an interface for enabling data communications between the exercise machine and the video system. Preferably, the video system is a cartridge-type video game system. The exercise machine includes a number of elements for measurement and control of the exercise activity. These elements communicate with the video system via the interface. Thus, the video system can collect, process and display exercise data, and can control the operation of the exercise machine such as, for example, by adjusting load resistance. In this manner, the exercise device capitalizes on the processing power of the video game system, and can be produced without a control computer or display, as has heretofore been required.

8. Video Game Exercise Protocols.

An additional object of the invention is to provide an exercise video system including an exercise machine having a variable resistance where exercise protocols are embedded in a video game. The protocols are effective to control the resistance in combination with a game scenario so as to accomplish a predetermined exercise objective by playing the game. In one embodiment, the video game display is generated to correspond to a predetermined resistance program while compensating for the rate of exercise of the user. For example, hills can be generated on the video system display that correspond to the resistance programs controlling the resistance in the exercise machine. At the same time, the display of the hills is adjusted to take into account the user's rate of exercise.

BRIEF DESCRIPTION OF DRAWINGS

FIG. 6 is a block diagram of the system of FIG. 1, showing the internal components of the interface module;

FIG. 7 is a timing diagram showing the timing relationship between the video system computer's clock signal and the internal clock signal used by the interface module;

FIG. 14 is a diagram illustrating the output of a video game having an embedded exercise protocol.

MODES FOR CARRYING OUT THE INVENTION

The invention is described with respect to the embodiments of FIGS. 1–14. While these embodiments incorporate the several features of the invention, it should be noted that in most cases these features can be practiced independently of one another. The primary features of the invention are discussed below, and are generally separated into sections under the captions Hardware Configuration, Communications Protocol, Multi-Modal Operation, Dynamic Control of Exercise Machine, Graphic Overlay Mode, Data Storage, Remote Control of Exercise Machine, and Video Game Exercise Protocols.

While the illustrated embodiment uses a video game system, it is understood that the term "video system" is intended to include any entertainment and educational products that employ graphic displays such as televisions, video monitors or liquid crystal displays (LCDs).

Hardware Configuration

Figure 1:
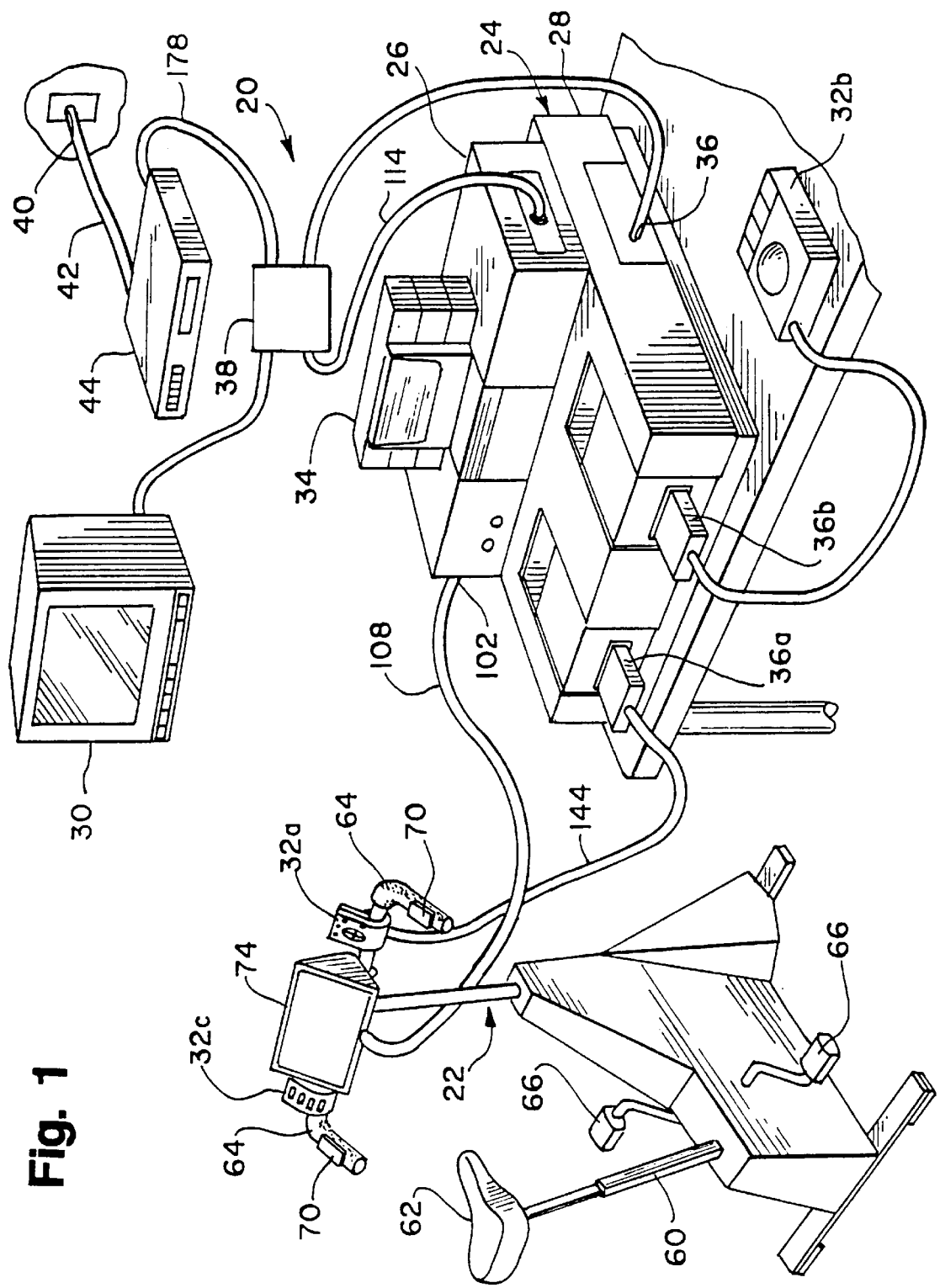
FIG. 1 is a perspective view of a system in accordance with the invention having an exercise machine, video system and interface module.
Figure 2:
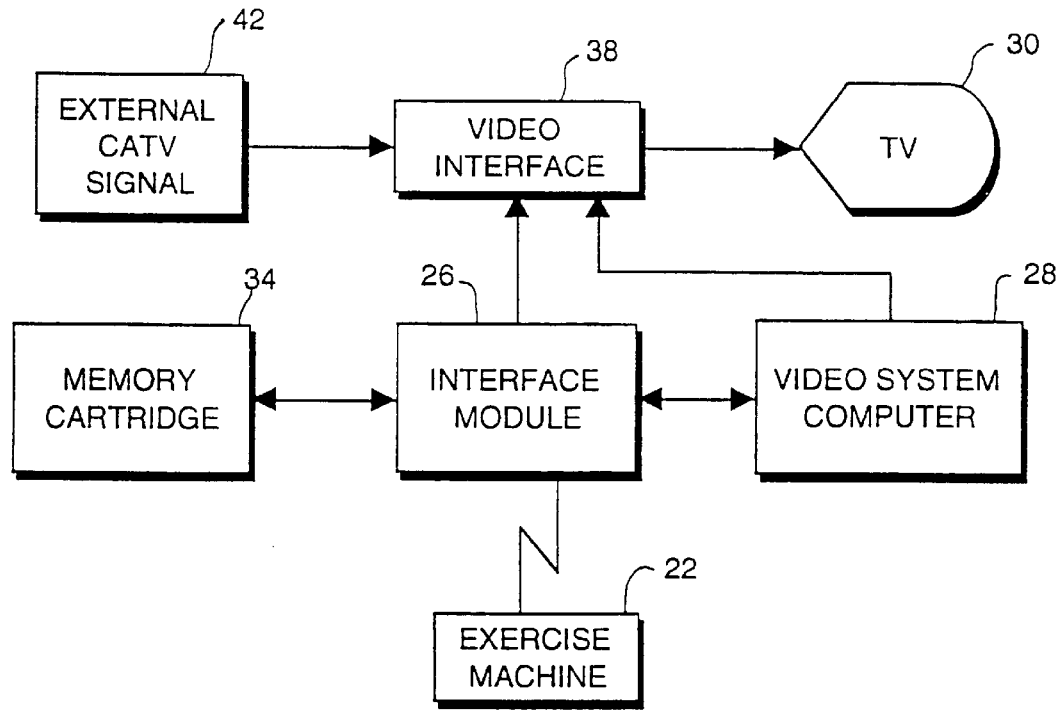
FIG. 2 is a block diagram of the system of FIG. 1.

FIG. 1 is a perspective illustration of an exercise-video system 20 in accordance with the invention. FIG. 2 is an accompanying block diagram. The system 20 includes an exercise machine 22, a video system 24 and an interface module 26. Each of these components is discussed below in greater detail. Generally speaking, however, the video system 24 communicates with the exercise machine 22 via the interface module 26, to effectively combine video entertainment with exercise.

Figure 3:
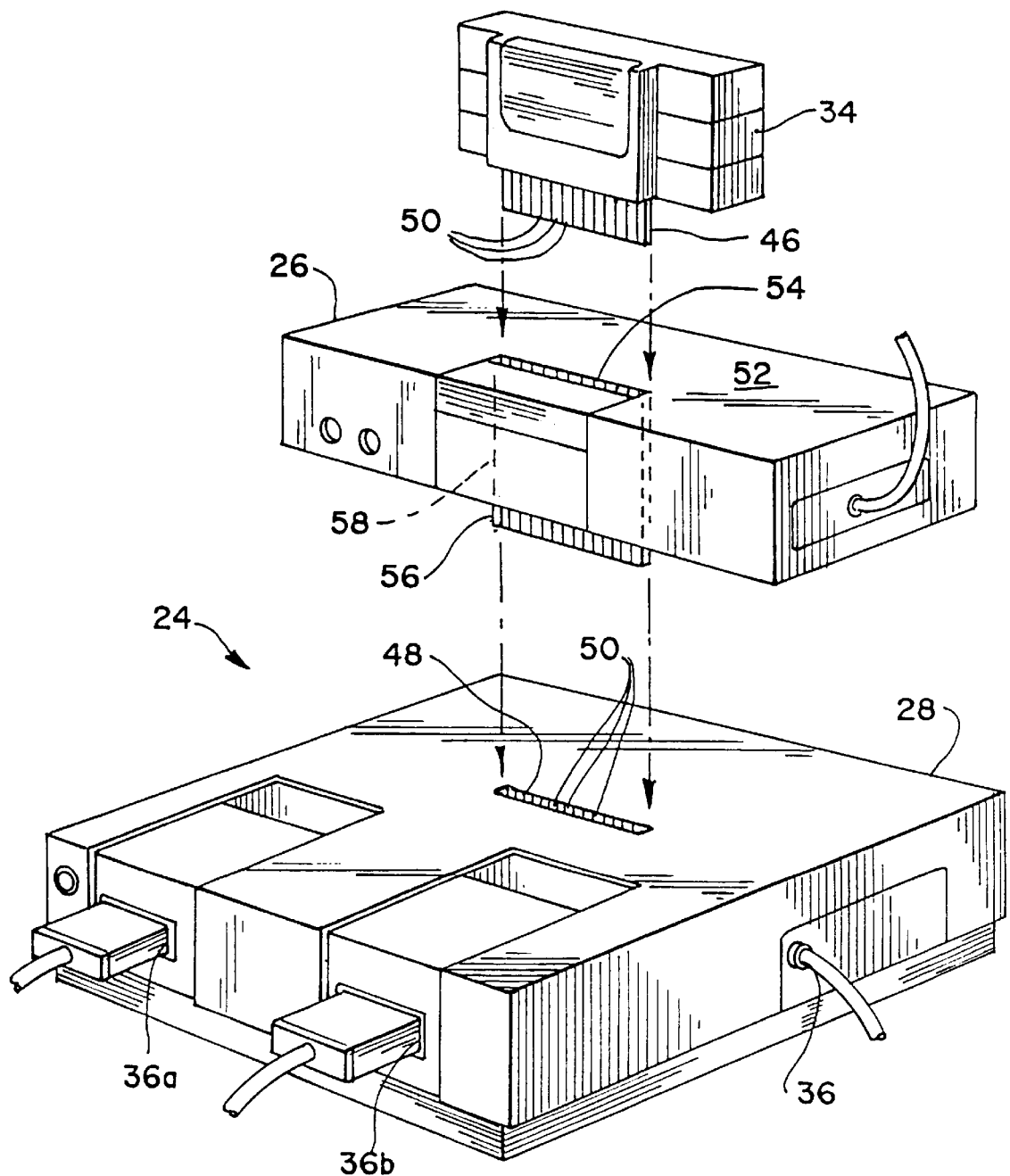
FIG. 3 is an exploded perspective view of the video system and interface module of FIG. 1.

Video System. Referring to FIGS. 1–3, the video system 24 is a cartridge-type video game system, such as commercially available under the trademarks Nintendo, Sega and Atari. The video system 24 includes a video system computer 28 or other control unit. The video system 24 is designed for use with, and typically sold separately from, a television 30. In some cases, the television 30 could be integral with the video system 24. However, for purposes of this specification, the video system 24 is considered separate from the television 30 unless otherwise specified.

The video system 24 also includes two game control peripherals (commonly called "joysticks") 32a and 32b, and a removable memory cartridge 34 containing a video game program. A third game control peripheral 32c is optionally coupled directly to the exercise machine 22.

While the illustrated embodiment uses the television 30 for a display, it should be noted that any graphic display device could be used, including video monitors and LCD displays, for example. Moreover, the invention can also be practiced using virtual reality techniques, including headset-type displays.

The video system computer 28 includes a video signal output 36 which is coupled to the television 30 via a video interface 38. As best seen in FIG. 1, a conventional wall outlet 40 provides an external cable TV (or "CATV") signal 42 which is routed first through a CATV tuner 44, and then to the video interface 38. The output of the video interface 38 is fed to the television 30.

The video interface 38 is discussed below in greater detail. Generally, however, it acts as a switch between the video signal output 36 and the output of the CATV tuner 44. Moreover, in accordance with the invention, the video interface 38 is coupled directly to the interface module 26 to allow exercise data and graphics to be overlayed onto the CATV signal 42.

The video system 24 is characterized in part by its modularity. For example, the game control peripherals 32a and 32b are releasably connected to video system computer 28 by jacks 36a and 36b, respectively. Likewise, the memory cartridge 34 is removable, to allow convenient reprogramming of the video system computer 28. While the primary application of video systems, such as the system 24, is for entertainment and video games, the invention may be practiced with other applications, such as educational or fitness training programs.

FIG. 3 is an exploded perspective view of the video system computer 28, the memory cartridge 34, and the interface module 26. It will be noted that the memory cartridge 34 includes a male connector 46 that conforms to a predefined standard. The video system computer 28 is equipped with a corresponding female connector 48 to allow the memory cartridge 34 to be conveniently plugged into to the video system computer 28. The male and female connectors 46, 48 have a number (in this case, sixty-two) of parallel lines 50 defining a video system bus for data, address, and control signals.

In accordance with the invention, the interface module 26 is interposed between the memory cartridge 34 and the video game computer 28. It includes a housing 52 having an upwardly opening female connector 54 adapted for receiving the male connector 46 of the cartridge 34, and a downwardly extending male connecter 56 adapted for engagement with the female connector 48 of the video system computer 28. As best seen in FIG. 6, a bus portion 58 inside the interface module 26 couples the memory cartridge 34 and video system computer 28, and acts as an extension of the video system bus.

The foregoing embodiment is provided for purposes of illustration. The invention may be practiced with other types of video systems, including personal computers, as well as systems which have a CD ROM or network interface in addition to or in lieu of the memory cartridge 34. Likewise, while the interface module 26 is preferably interposed between the video system computer 28 and memory cartridge 34, other configurations are possible. For example, the interface module 26 could be coupled with the video system bus through an expansion slot, jack or other aperture in the housing of video system computer 28. Alternatively, the interface module 26 could be internal to the video system computer 28, and could be coupled electrically or via light, radio or other suitable media.

Exercise Machine. The exercise machine 22, as illustrated in FIG. 1, is a stationary exercise bicycle, such as described in U.S. Pat. No. 4,358,105. The exercise machine 22 has a frame 60, a seat 62 on which a user may sit, handlebars 64 and pedals 66, which the user may engage for repetitive exercise movement. The invention may also be practiced with other types of exercise machines, such as rowing machines, skiing machines, stair climbing simulators, and treadmills, for example.

Figure 4:
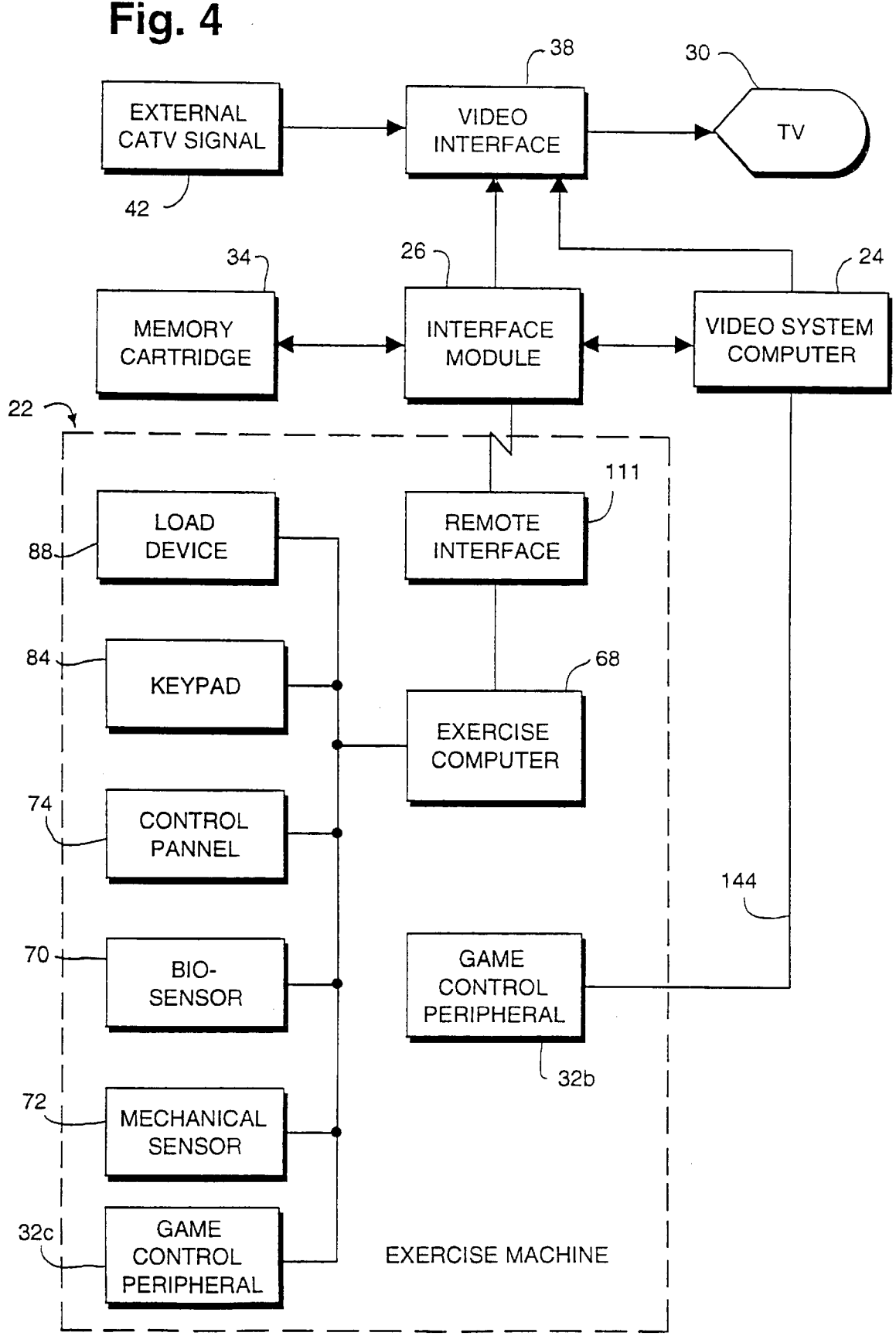
FIG. 4 is a block diagram of the system of FIG. 1, showing in greater detail the components of the exercise machine.

The components of the exercise machine 22 are illustrated in FIG. 4. The exercise machine 22 includes an exercise computer 68, which is a Motorola brand 68HC05 microcontroller. Alternatively, any suitable control unit may be used. As best seen in FIG. 4, the exercise computer 68 is operatively associated with a number of sensors and devices, namely biosensors 70, a mechanical sensor 72, a control panel 74 and an optional game control peripheral 32c. The biopotential and mechanical sensors such as sensors 70, 72 generate data related to the user's exercise movement. This data could include heart rate, pedal rpm, calorie consumption or other exercise conditions. Generally, mechanical sensors are coupled directly to the exercise machine 22, while biosensors may be coupled to the user or the exercise machine.

The mechanical sensor 72 is a tachometer, and is associated with the pedals 66 for generating a pedal rpm signal. Game control peripheral 32c is optionally mounted to the handlebar 64 for providing user-controlled game input. The biosensors 70 are mounted to the handlebars 64 for detecting the user's heart rate. An example of a suitable heart rate detection system can be found on the Lifecycle® 9500 HR brand stationary exercise bicycle, available from Life Fitness of Franklin Park, Ill., USA. Alternatively, biosensors 70 can be clipped to the user's ears, mounted to the user's chest or affixed on game control peripherals 32a and 32c. Optionally, the biosensors 70 may communicate with the interface module 26 via a radio signal and/or an analog signal on one or more dedicated lines (not illustrated).

Figure 5:
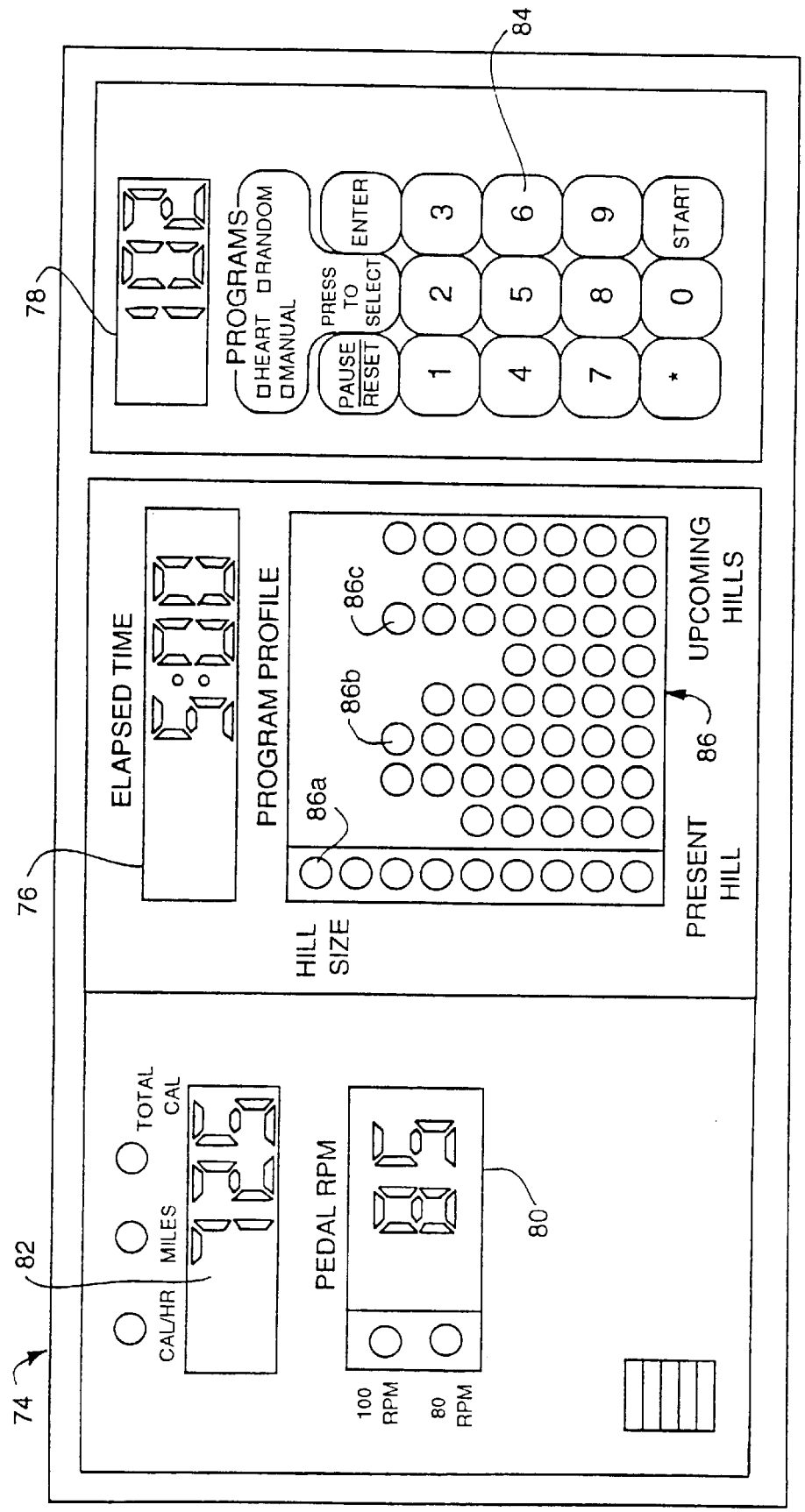
FIG. 5 is a plan view of the control panel of the exercise machine of FIG. 1.

The control panel 74 displays exercise data such as elapsed exercise time, total calorie consumption, heart rate, and pedal rpm. FIG. 5 illustrates a plan view of the control panel 74. The control panel interfaces with the exercise computer 68 in any suitable manner, such as by serial or parallel interface, and includes displays for elapsed time 76, heart rate 78, pedal rpm 80 and calorie consumption 82.

The control panel 74 also includes a keypad 84 for accepting user input. User input can include physiological data (such as sex, age and weight) that is useful for managing various types of exercise programs. It can also include a user-selected effort level, which can be used to determine or scale the load resistance imposed on the user.

The control panel 74 may include a program profile display 86, which provides a scrolling bar graph of current and upcoming load resistance values. The program profile display 86 includes columns of LEDs, several of which are designated in FIG. 5 by reference numerals 86a–86c. Each of the columns 86a–86c graphically displays current and upcoming values of load resistance which will be imposed on the user. These values are stylized as "hill size." The magnitude of each load value is represented by successive illuminating columns of LEDs to define a vertical bar graph. The current value is in the far left-hand column 86a of the program profile display 86, and the future values are arranged in chronological order from left to right in the remaining columns 86b–86c. As the program profile display 86 is updated, the represented load values appear to scroll across the display 86 from right to left.

The pedals 66 are drivingly connected (such as by chains or belts, not illustrated) to a load device 88, which in this case is an alternator. Alternator 88 imposes physical drag or load resistance against the user's exercise movement. While the alternator 88 is the preferred load resistance mechanism, an eddy-current brake or other suitable device may be used. The alternator is responsive to a load control signal 90 generated by the exercise computer 68 for varying the level of resistance imposed on the user. In this manner, it is possible to regulate the physiological intensity of the user's exercise movement. An example of this technique is disclosed in U.S. patent application Ser. No. 07/881,918 filed May 12, 1992.

There are a number of techniques for controlling the load resistance of the alternator 88. One technique especially suited to computer controlled exercise machines is pulse width modulation. Accordingly, the exercise computer 68 applies a binary pulse train to the alternator's field coil (not illustrated). By varying the duty cycle of the pulse train, the exercise computer 68 can control the torque resistance imposed by the field coil on the alternator's driven coil (not shown).

Interface Module. As explained below in greater detail, the interface module 26 allows the video system computer 28 to communicate with the exercise machine 22. Thus, data generated by the exercise machine 22 (such as heart rate and pedal rpm) is accessible to the video system computer 28. Consequently, the user can play an interactive video game in which the user's exercise performance affects game outcome.

Moreover, the video system computer 28 can instruct the exercise machine 22 to vary load resistance of the alternator 88 in accordance with the game software resident on the memory cartridge 34. For example, in a video game involving a simulated bicycle race over hilly terrain, the video game computer 28 can increase or decrease the exercise machine's 22 load resistance in accordance with the grade of the simulated terrain and/or the user's exercise performance.

Referring to FIG. 6, the internal structure of the interface module 26 is illustrated in greater detail. The major elements of the interface module are: the internal bus 58, which has data, address, control and power lines; an addressable asynchronous communications port 94; a static random access memory ("SRAM") 96; a video port 98 which allows a byte of data to be overlaid on the television 30 via the video interface 38; and a network interface 99 which allows the video system computer 28 to communicate via modem or the like with remote devices such as network 101. Each of these components is coupled to the address and data lines of the bus 58 so that it is accessible by the video system computer 28.

The SRAM 96 is eight kilobytes in size, and preferably includes a battery backup 100. Coupled to the video system computer 28 via the address and data lines of the bus 58, the SRAM 96 allows the video system computer 28 to store and retrieve data, including exercise-related data. In this manner, data can be maintained by the system 20 even when memory cartridge 34 is changed. This feature is particularly useful for users who may want to track exercise data relating to past exercise sessions without having to always use the same memory cartridge (i.e., play the same video game).

The communications port 94 features an RS-232 connector 102, and conversion circuit 104 and an asynchronous communication interface chip ("ACIA") 106. A cable 108 (best seen in FIG. 1) connects the RS-232 connector 102 to the exercise machine 22. Alternatively, data could be communicated via light, radio or other suitable media. Data received from the exercise machine 22 enters the interface module 26 via the connector 102. The conversion circuit 104 converts the incoming data signal from RS-232 voltage to TTL voltage. The converted data is then fed serially from the conversion circuit 104 to the ACIA 106. The ACIA 106 accumulates the data in an internal register (not illustrated) so that it is available in parallel format. Likewise, data stored in the ACIA 106 can be transmitted to the exercise machine 22 via the conversion circuit 104 and RS-232 connector 102. The exercise machine 22 includes a remote communications interface 111 (best seen in FIG. 4) which is comparable to the communications port 94. The remote communications interface 111 enables the exercise computer 68 to send and receive data on the RS-232 channel defined by the cable 108.

The conversion circuit 104 includes a MAX232, available from Maxim Integrated Products of Sunnyvale, Calif., USA.

The ACIA 106 is a model 6551 available from Rockwell International Corp., USA. While RS-232 standard communication is preferred, any suitable standard may be used.

The ACIA 106 is coupled to the address and data lines of the bus 58 so that the video system computer 28 can read and write data bytes to and from the ACIA 106. When the interface module 26 is first activated, the video system computer 28 initializes the ACIA 106 to communicate at 9600 Baud and to generate a hardware interrupt ("IRQ") signal each time it receives a byte of data. The communications protocol and software used in the illustrated embodiment is discussed below in greater detail.

The video port 98 enables the video system computer 28 to write data to the video interface 38, which in turn overlays the data on the CATV video signal 42. The video port 98 is a data latch coupled to the address and data lines of the bus 58, as best seen in FIG. 6. Four bits of the video port 98 are each coupled to a separate one of four lines 114. The four lines 114 are in turn coupled to the video interface 38. Three of the four lines 114 are for timing and control. The fourth is for serial transmission of data. Because this data is transmitted serially, the video system computer 28 must write eight times to the video port 98' in order to transmit one eight-bit byte to the video interface 38. Alternatively, an additional interface chip, such as ACIA 106, could be used which would accept the video data from the video system computer 28 as a single byte. The video overlay function is discussed below in greater detail.

The interface module 26 includes two additional components which prevent potential hardware conflicts between the interface module 26 and the memory cartridge 34. The first additional component for preventing hardware conflicts is a clock divider 118. The clock divider 118 is a JK flip flop, having as a clock input the system clock signal SYSCLK generated by the video system computer 28. The clock divider 118 is arranged to generate an output clock pulse signal 120, which has a frequency that is one-half that of the input signal SYSCLK.

The reduced-frequency clock pulse signal 120 is fed into the clock input of the ACIA 106, so that each clock cycle of ACIA operation actually has a duration equal to two clock cycles of the video system computer 28. In some cases, the clock speed of the video system computer is too fast to enable successful access of the ACIA 106. By dividing the ACIA's 106 clock frequency to one-half the frequency of the video system's clock signal SYSCLK, the ACIA 106 has adequate time to accept or provide data bits onto the data lines of bus 58.

FIG. 7 is a diagram illustrating this timing relationship. Referring to FIG. 7, at time $t_0$, the video system computer 28 generates a first clock pulse 122, and places data and address information onto the data and address lines of the bus 58. At the same time, the interface module clock divider 118 generates an ACIA clock pulse 124. This ACIA clock pulse 124 is asserted through time $t_2$, when the video system computer 28 generates a second clock pulse 126. At time $t_3$, both the single ACIA clock pulse 124 and the second computer clock pulse 126 are terminated.

In practice, the actual data byte to be read or written to the ACIA should be placed onto the bus between the falling edges at time $t_1$ and $t_3$ of the first and second clock pulses 122 and 126. In video systems with eight-bit buses and sixteen-bit words, this can be accomplished by placing the subject byte in that half of the word which the video system computer 28 last places onto the bus 58.

The second additional component for preventing hardware conflicts is an address decoder 128. The address decoder 128 is coupled to the address lines of the bus 58 and functions as a chip-select circuit. Each of the above-mentioned devices (communications port 94, SRAM 96, and video port 98) is associated with a predetermined address or range of addresses. When the video system computer 28 places one of these addresses on the address lines of the bus 58, the address decoder 128 asserts that one of the chip enable outputs (illustrated in FIG. 6 as RAMSEL, ROMSEL, VIDSEL, and COMSEL) which enables the device corresponding to the address. For illustration, the RAMSEL signal enables the SRAM 96; the VIDSEL signal enables the video port 98; the COMSEL signal enables the communications port 94 and clock divider 118; and ROMSEL signal enables the memory cartridge 34. If the optional network interface 99 is used, the address decoder 128 should provide an additional chip enable output.

The address decoder 128 is also coupled to a control line SELECT, which is shown in FIG. 6 apart from the other control lines of the bus 58. In some cases, the video system computer 28 may assert the SELECT line when it is addressing memory locations in the memory cartridge 34. To avoid a possible hardware conflict, the SELECT line does not run directly from the connector 56 to the connector 54. Rather, it terminates at the address decoder 128. The address decoder 128 circuit asserts the ROMSEL signal (to enable the memory cartridge 34) when the video system computer 28 has asserted the SELECT line and none of its other chip enable lines are asserted. Thus, to the memory cartridge 34, the ROMSEL signal is interpreted as though it were the SELECT signal line.

Communications Protocol

Figures 10, 11, 12:
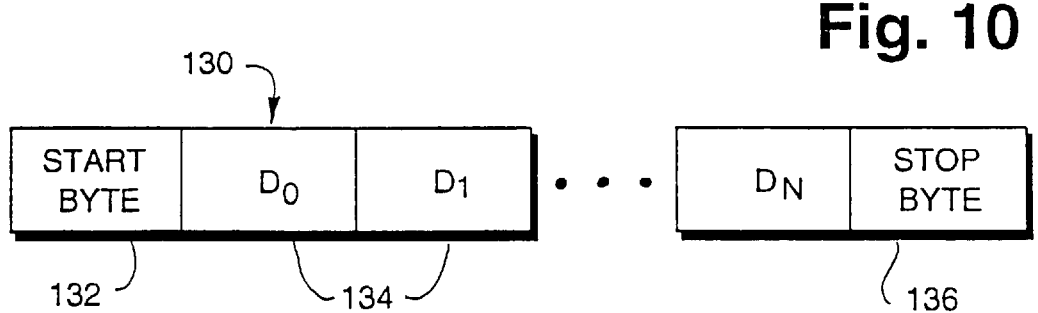
FIG. 10 is a diagrammatic illustration of a communications data packet.
FIG. 11 is a diagram showing the contents of a status data packet transmitted from the exercise machine to the video system of FIG. 1.
FIG. 12 is a diagram showing the contents of a command data packet transmitted from the video system to the exercise machine of FIG. 1.

Referring now to FIGS. 10–12, the communications protocol between the video system 24 and the exercise machine 22 is now considered in greater detail. With both units 22,24 powered on and initialized, the exercise machine 22 and video system 24 can periodically exchange data, allowing the video system computer 28 both access to exercise data and the ability to control the exercise machine 22. Optionally, the data can be encrypted to prevent use of counterfeit interface modules.

This communication is made possible by the interface module 26, discussed in detail above. The interface module 26 is coupled to the bus 58 so that the video system computer 28 can send and receive data packets such as the generalized communication packet 130 of FIG. 10. Each data packet includes a start byte 132, a predetermined number of data bytes 134 following the start byte 132, and a stop byte 136. The start byte 132 has a ninth bit asserted. (The parity bit can be used for this purpose.) When the communications port 94 in the interface module 26 detects that this ninth bit is asserted, it generates an interrupt signal so that the video system computer 28 can process the remaining data bytes. Likewise, when the remote communications interface 111 in the exercise machine 22 detects that the ninth bit is asserted, it too generates an interrupt signal so that the exercise computer 68 can process the incoming data packet.

In the illustrated embodiment, communication is controlled by the exercise machine 22, which every 100 milliseconds transmits a communication packet 130 having a status data packet 138 as shown in FIG. 11. When the ACIA 106 in the interface module 26 receives a start byte 132 transmitted by the exercise machine 22, it asserts the IRQ signal, generating a hardware interrupt. The interrupt enables the video system computer 28 to process the incoming transmission. Each successive data byte of the status data packet 138 causes the ACIA 106 to generate an interrupt. The video system computer 28 can then read the byte from the ACIA 106 via the address and data lines of the bus 58.

When the stop byte 136 is received, the video system computer 28 transmits a communications packet 130 having a command data packet 140 as shown in FIG. 12. When the remote communications interface 111 on the exercise machine 22 receives the start byte 132 of the communications data packet 130 transmitted by the video system computer 28, it too asserts an interrupt signal. The interrupt enables the exercise computer 68 to process the incoming command data packet 140.

The status data packet 138 transmitted by the exercise machine 22 includes the following bytes: a start byte (including an address and ninth start bit); data bytes $D_1$ through $D_5$; and a stop byte (including a checksum and ninth stop bit). The start byte includes an arbitrary address that is preassigned to interface module 26. Start bytes which have a different address are ignored by the ACIA 106. The data byte $D_0$ is a status byte. The data bytes $D_1$ through $D_4$ are exercise data. In this case, the exercise data includes pedal RPM, elapsed time in minutes and seconds, user-selected level and machine type. Other exercise data may be transmitted depending on the nature and capabilities of the exercise machine 22. The machine type byte $D_5$ indicates the type of exercise machine, and is discussed below in greater detail. The stop byte 136 is a checksum, and includes a ninth stop bit.

The status byte 138 has five predefined values each corresponding to a different one of the following status conditions: (i) NULL status; (ii) READY status; (iii) RUNNING status; (iv) PAUSING status; and (v) ENDING status. The NULL status means "no status." The READY status means that the exercise machine 22 is operating and ready to begin interactive communication with the video system computer 28. The RUNNING status means that the exercise machine 22 is engaged in interactive communication, and is accepting command data packets 140 from the video system computer 28. The PAUSING status means that the exercise machine 22 is pausing. The ENDING status means that the exercise program has terminated, and the exercise computer 68 is displaying exercise data.

In response to receipt of a status data packet 138, the video system computer 28 transmits the command data packet 140 via the interface module 26 including the following bytes: start byte (having an address and ninth start bit); a command byte $D_0$; a load value byte $D_1$; display data bytes $D_2$ through $D_5$; and a stop byte (having a checksum and a ninth stop bit).

The start byte of the command data packet 140 includes an arbitrary address that is preassigned to the exercise machine 22. Start bytes which have a different address are ignored by the exercise machine 22. The load value $D_1$ is interpreted as the value of the load resistance to be imposed on the user by the alternator 88, and is discussed below in greater detail. The stop byte 136 is a checksum, with an additional stop bit. The command byte $D_0$ has five predefined values, each corresponding to a different one of the following five commands: (i) NULL command (ii) INITIALIZE command; (iii) UPDATE command; (iv) PAUSE command; (iv) TERMINATE command; and (v) ABORT command.

The NULL command causes no action to be taken by the exercise machine 22. The INITIALIZE command instructs the exercise machine 22 to initialize (i.e., reset) the exercise data (such as total calories consumed) and to begin interactive operation. During interactive operation, the exercise computer 68 relinquishes control of the load resistance and program profile display 86, and abides by the commands issued by the video system computer 28. The PAUSE command causes the exercise computer 68 to place the exercise machine 22 in a pause mode, such as to allow the user to momentarily dismount. The TERMINATE command causes the exercise machine 22 to set load resistance to its lowest level, and display exercise data. The ABORT command causes the exercise machine 22 to immediately terminate interactive operation, and resume stand-alone operation.

The UPDATE command instructs the exercise computer 68 to update the load control signal 90 and the program profile display 86 with the data bytes $D_1$ through $D_5$ contained in the command data packet 140. As discussed earlier, the exercise computer 68 controls the alternator 88 by pulse width modulation of the load control signal 90. When the exercise computer 68 receives an UPDATE command, it adjusts the duty cycle of the load control signal 90 in accordance with the value of the load byte $D_1$.

The exercise computer 68 also updates the program profile display 86 in accordance with the data bytes $D_2$ through $D_5$. In practice, each byte $D_2$ through $D_5$ corresponds to one of the predefined columns of the program profile display matrix 86, and each bit of each byte corresponds to one of the LEDs in that column. The state of each particular bit determines whether or not its corresponding LED is illuminated. Depending on the number of columns in the program profile display 86, additional or fewer data display bytes must be used.

A typical dialogue between the exercise computer 68 and the video system computer 28 begins when the exercise machine 22 is initially powered up. At that time, the exercise computer 68 begins transmitting (every 100 milliseconds) a status data packet 138 with the status byte indicating a READY status. At some point in time, the user activates the video system 24, whereupon the video system computer 28 begins receiving the status data packet 138 broadcast by the exercise machine 22.

Via the interface module 26, the video system computer 28 responds to the first received status data packet 138 by transmitting a command data packet 140 with the command byte indicating an INITIALIZE command. This causes the exercise machine 22 to begin interactive operation. The video game computer 28 does not necessarily have to issue the INITIALIZE command immediately. Rather, initialization can be in response to user input (such as via the game control peripheral 32a). Alternatively, the video system computer 28 can broadcast the INITIALIZE command, but the exercise computer 68 can be programmed to ignore it until instructed by the user (via the exercise keypad 84) to begin interactive operation.

Once the exercise machine 22 receives and accepts the INITIALIZE command, it begins broadcasting a status data packet 138 having a status byte $D_0$ indicating a RUNNING status. When the video system computer 28 receives this status, it transmits an UPDATE command, causing the exercise computer 68 to update the load control signal 90 and program profile display 86 in accordance with the load and display data ($D_1$ through $D_5$) in the command data packet 140. The exercise machine 22 continues to broadcast a RUNNING status every 100 milliseconds, and the video system computer 28 continues to respond with successive UPDATE commands.

At some point, the user may (via the keypad 84) place the exercise machine 22 into a pause status. In pause status, load resistance is set to its lowest value, giving the user an opportunity to rest or dismount. When the exercise machine 22 is in pause status, the exercise computer 68 transmits a status data packet 138 having a status byte $D_0$ indicating the PAUSE status. When the video system computer 28 receives the PAUSING status communications protocol. The modes described in this section relate to high-level system operation, whereas the status conditions described in connection with the communications protocols relate to the details of data communication between the exercise machine 22 and the video system 24.

In Exercise Mode and Graphic overlay Mode, the video system computer 28 is interfaced to the exercise machine 22 for receiving exercise data and transmitting load and display commands. It is to the implementation of these modes that the above-described interface module 26 and communications protocol are directed.

Contrastingly, in Game Mode, the exercise machine 22 and video system 24 operate separately, as stand-alone units. It will be observed that a user may exercise while playing a video game in Game Mode. To facilitate this, one of the video game's game interface peripherals 32a is mounted to the handlebars 64 of the exercise machine 22. The game interface peripheral 32a is wired via a cord 144 to the video system computer 28, and can therefore function independently of the interface module 26. As discussed above, the third game control peripheral 32c can be mounted on the handlebars 64 and can be connected to the video system 24 via the interface module 26. As part of the exercise machine 22, however, the third game control peripheral cannot be used in Game Mode.

To accommodate this multi-modal operation, the software encoded in the memory cartridge 34 is written to accept input from the exercise machine 22 (via the interface module 26) when in Exercise Mode and Graphic Overlay Mode, and to accept input from the game control peripherals 32a and 32b when in the Game Mode. In this manner, memory cartridge 34 has maximum flexibility for use in standard video games and other programs, whether or not equipped or used with the interface module 26. It is also possible for the program on memory cartridge 34 to accept input from both the game control peripherals 32a, 32b and the exercise machine 22. This feature is particularly useful when two users are playing a video game, but only one is using the exercise machine 22. In this respect, the program operates in Game Mode with respect to the user who is not on exercise machine, and in Exercise Mode with respect to the user who is on exercise machine 22.

Figure 13:
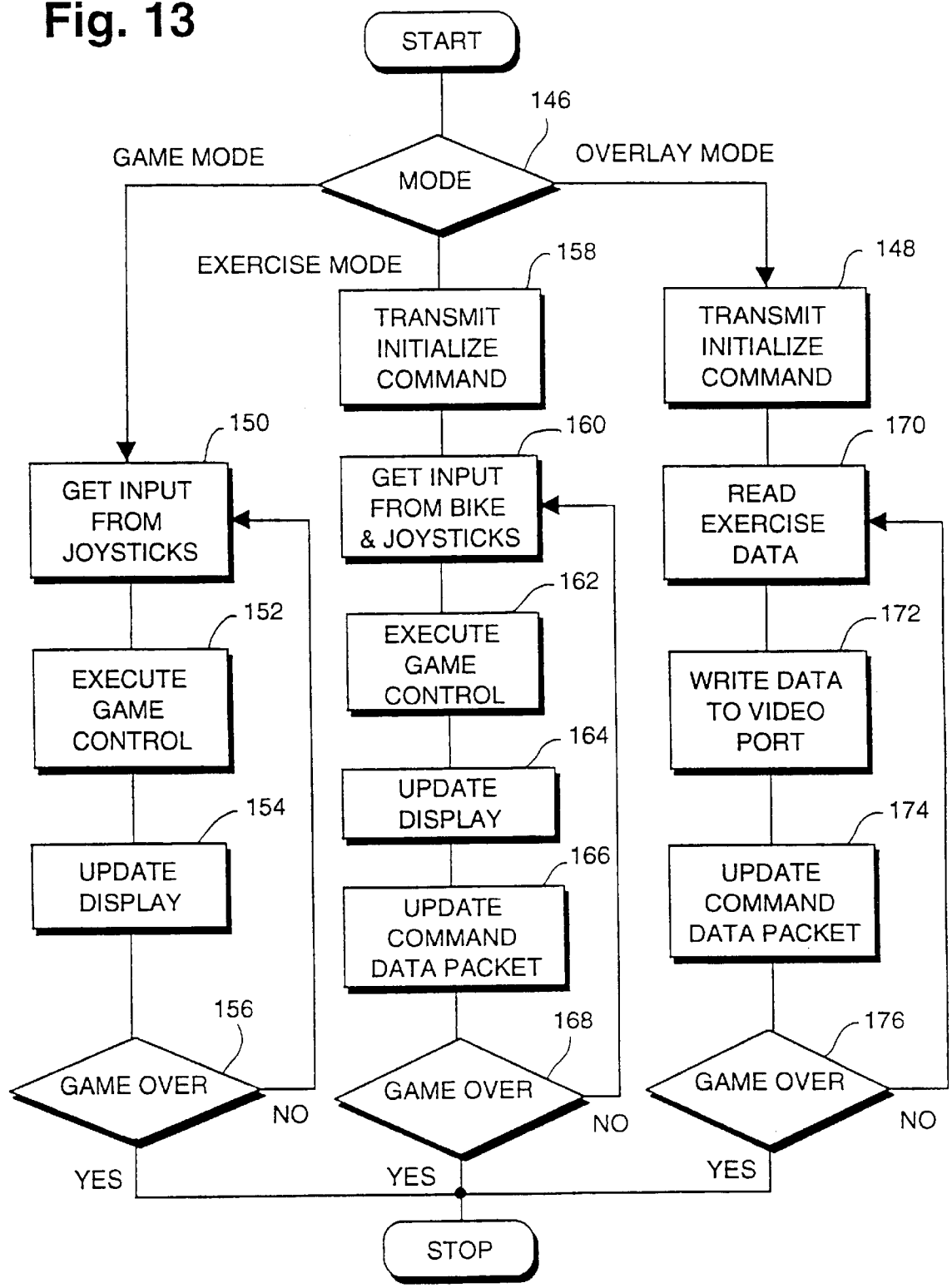
FIG. 13 is a logic flow chart showing the generalized operation of software executed by the video system of FIG. 1.

The flow chart of FIG. 13 illustrates the generalized operation of the software of memory cartridge 34 executed in the video system computer 28. At a block 146, the video system computer 28 accepts a mode selection from the user. This may be accomplished under software control via one of the game control peripherals 32a and 32b, or by an external hardware switch (not illustrated). The video system computer 28 determines at block 146 which mode is selected. If Graphic Overlay Mode is selected, control moves to a block 148. Details of Graphic Overlay Mode are discussed below.

If Game Mode is selected, the video system computer 28 reads user input from the game control peripherals 32a and 32b at a block 150, executes game control at a block 152, and updates the display on the television 30 at a block 154. Although in the illustration, the software is directed toward an interactive video game, other applications can be used, including, for example, a fitness trainer. At a decision block 156, if the game is over, the program terminates. Otherwise, control returns to the block 150, and processing at blocks 150 through 156 is repeated.

If the Exercise Mode is selected, the video system computer 28 transmits on INITIALIZE command to the exercise machine 22 at a block 158. The protocol of this communication is discussed above. At a block 160, the video system computer 28 reads input data from the exercise machine 22 (via the interface module 26) and game control peripherals 32a and 32b. At a block 162, the video system computer 28 executes game control. At a block 164, the video system computer 28 updates the video display on the television 30 to reflect changes in game state as a result of the processing at the block 162. At a block 166, the video system computer 28 determines the contents of the next command data packet. At a decision block 168, if the video game is over, the program terminates. Otherwise, control returns to the block 160, and processing at the blocks 160 through 168 is repeated.

It is understood that the processing depicted in the blocks 158 through 168 represents only one of many possible approaches. For example, these steps 158 through 168 may be performed in a different order or concurrently, depending on the nature of the video system 24 and the specific program executed thereon. The step 162 of executing game control at the blocks, refers to the idea that the video system computer 28 will update the state of the video game or other program in response to past and current user input and the passing of time. For example, if a video game depicts a player as a bicyclist racing down a highway, the step 162 of executing game control might include a determination of what speed the player's opponents will pedal as a function of past and current user input.

Dynamic Control of Exercise Machine

When operating in the Exercise Mode, the video system computer 28 may adjust load resistance imposed by alternator 88 in accordance with the outcome of the video program. For the purpose of illustration, it is assumed that the video system computer 28 is executing a video game program which generates an animated display (on the television 30) of a race over terrain of varying grade and quality. The video system computer 28 adjusts the load resistance of alternator 88 in accordance with the varying terrain depicted and the user's actions. Thus, for example, if the terrain depicted on the television 30 has an increasing grade, then the video system computer 28 increases the load resistance of alternator 88.

The difficulty in existing systems is that changes in actual load resistance may not be properly coordinated with changes in the depicted terrain or other video display. This discrepancy may arise because various exercise machines have different operating characteristics depending on the type of machine and the type of load device used in that machine. For example, an exercise bicycle using an alternator for load resistance has different operating characteristics than an exercise bicycle using an eddy current brake, or a stair climber using a band brake.

The operating characteristic of greatest interest is the load response. Load response refers to the time delay between changes in the load control signal 90 and changes in the actual load imposed on the user by the alternator 88. Fortunately, the load response of the alternator 88 is almost instantaneous. However, the load response in an eddy current brake, for example, may be delayed by several seconds.

If actual load experienced by the user is to reflect the changes in simulated terrain (or other visual display), then it is important that the change in load occur virtually simultaneously with the depicted changes in terrain (or other visual display). The realism (and, ultimately, enjoyment) of the game is diminished when the user's visual input (such as, for example, the grade of a simulated hill) does not jibe with the sensory input of load resistance.

In cases where load response is instantaneous, video system computer 28 can adjust the load control signal 90 concurrently with the changes in video output (such as the depicted grade of terrain). Where the load response is delayed (such as occurs with eddy current brakes), the video system computer 28 adjusts the load control signal 90 in advance of the change in video output. For example, if the load response is a five second delay, the video system computer 28 begins to increase the load control signal 90 five seconds in advance of the upcoming hill.

Because the operating characteristics (such as load response) vary from exercise machine to exercise machine, it was initially unclear as to how the video system computer 28 would be able to control different types of devices. One solution is to have each memory cartridge 34 programmed to handle a particular type of exercise machine. Under this approach, however, cartridges designed for eddy-current-based machines would function poorly when used with alternator-based exercise machines. This lack of flexibility is commercially impractical.

In the illustrated embodiment, this problem is solved by including in the status data packet 138 (see FIG. 11) a machine type data byte $D_5$. This type data byte contains a code corresponding to the type of exercise machine 22. For example, an eddy-current-based bicycle is assigned type number "001," while an alternator-based stair climber is assigned type number "002." A table (not shown) in the memory of the memory cartridge 34 associates each type with its assigned characteristic. In this manner, the video system computer 28 can adjust the load (or other) control signal 90 in accordance with the load response (or other operating characteristic) associated with the particular type of exercise machine 22.

While practical, one difficulty with this approach is that it may not be able to accommodate new type of exercise machines whose operating characteristics do not fall within an existing type. To overcome this problem, the exercise device may transmit a special data packet referred to as the operating characteristic specification ("OCS") data packet. The OCS data packet is transmitted by the exercise machine 22 in response to the video computer 68 sending an INITIALIZE command.

The OCS data packet includes the following bytes: start byte (having an address and ninth start bit); status byte $D_0$ (operating characteristic parameters $D_1$–$D_5$); and a stop byte (having a checksum and a ninth stop bit). The protocol for communicating data packets is discussed above under the heading "Communication Protocols".

Where the OCS is to be used, the status byte can take a sixth value (in addition to the five values discussed above) which indicates that the status data packet is an OCS data packet. The operating characteristic parameters are parameters which specify the operating characteristics. One possible set of parameters is: type of exercise movement (reciprocal or rotary, independent or dependant); limbs exercised (legs or arms); load response (in seconds delay); type of resistance (mechanical, eddy current, alternator). Alternatively, other descriptions can be used.

While quite powerful, this OCS approach is still subject to the possibility that exercise equipment will be developed that is so novel that the predefined parameters are insufficient. To overcome this contingency, a third alternative is provided, wherein the command data packet 140 (see FIG. 12) includes additional data bytes (not shown) specifying upcoming load values. The exercise computer then determines internally when the load control signal 90 should be adjusted in accordance with the upcoming load values.

Graphic Overlay Mode

In some cases, a user of the system may want to use the television 30 to watch prerecorded video cassettes, CATV, broadcast TV or other external video signal. In these cases, it is desirable that the user's exercise data be periodically displayed on the television 30 over the external video signal. To accomplish this objective, the system 20 includes a Graphic Overlay Mode. In Graphic Overlay Mode, the video system computer 28 does not generate a video output. Rather, its main tasks are to manage communications with the exercise machine 22, and to output digital exercise data to the video port 98 for superimposing display on the television 30. In Graphic Overlay Mode, the video system computer 28 can also control load resistance imposed by the alternator 88 of exercise machine 22 in accordance with any suitable exercise program.

In practice, the software necessary for implementing the Graphic Overlay Mode can be incorporated as a routine on the memory cartridge 34. As shown in the flow chart of FIG. 13, when initiating operation of the video system 24, the user is given the choice of three operational modes, including the Graphic Overlay Mode. The user may assert this choice either via an external hardware switch (not shown) or via one of the game control peripherals 32a, 32b under program control. Referring to FIG. 13, if the user selects the Graphic Overlay Mode, then control moves to a block 148, where the video system computer 28 transmits the INITIALIZE command to the exercise machine 22 in accordance with the communications protocol discussed above. At block 170, the video system computer 28 reads the exercise data which it receives from the exercise machine 22. At a block 172, the video system computer 28 writes data to the video port 98. At a block 174, the video system computer 28 updates the command data packet 140. In this regard, the video system computer 28 can adjust the load resistance of alternator 88 in accordance of any suitable exercise program. At a block 176, if the exercise program is over, the Graphic Overlay Mode terminates. Otherwise, control returns to the block 170, and the blocks 170 through 176 are repeated.

It is understood that the Graphic Overlay Mode is an aspect of the invention that can be practiced with hardware configurations and communication protocols other than those illustrated above. Specifically, the video port 98 could be disposed within the exercise machine 22 for direct access by the exercise computer 68. In this case, the exercise computer 68 (as opposed to the video system computer 28) writes exercise data to video port 98.

Figure 8:
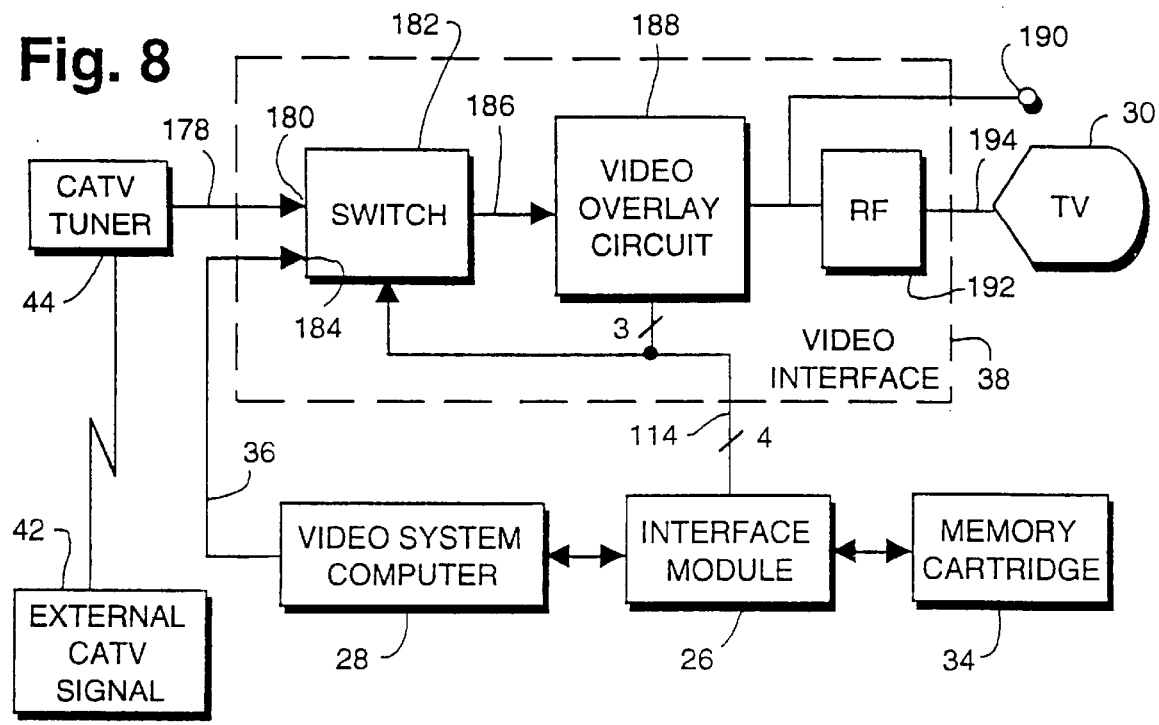
FIG. 8 is a block diagram of the system of FIG. 1, showing the internal components of the video interface.

To implement the Graphic Overlay Mode, the video interface 38 has been provided. FIG. 8 illustrates the video interface 38 in greater detail. In this illustration, the television 30 is used to display the external CATV signal 42. Alternatively, the television 30 could be used to display a video signal from a VCR or compact disk player, or to display a broadcast television signal. The external CATV signal 42 is received in the user's home by the CATV tuner 44, which outputs a video signal 178. This video signal 178 is fed into first input 180 of a switch 182. The switch 182 includes a second input 184 for receiving the output 36 of the video system computer 28. The switch 182 has an output 186, and, by means of a mechanical or electronic switch, selectively couples the first or second input 180, 184 to the output 186.

Preferably, the switch 182 is electronically activated by one of the four control lines 114 emanating from the video port 98 of the interface module 26 (see also, FIG. 6 and discussion above relating to video port 98). Thus, the video system computer 28 can, under software control, actuate switch 182 via one of the lines 114 to selectively enable either the CATV signal 42 or the video output 36. In Graphic Overlay Mode, the video system computer 28 enables the CATV signal 42 and at the same time writes data to the video port 98 for superimposition over the CATV signal 42.

While the multi-modal operation of exercise video system 20 (discussed above in connection with the flow chart of FIG. 13) contemplates that the Graphic Overlay Mode is selected by the user at the beginning of operation of the system 20, alternatives are possible. For example, the video system computer 28 could toggle back and forth between Exercise Mode and Graphic Overlay Mode. This would enable a user playing a video game, for example, to suspend the video game and watch regular CATV programming in Graphic Overlay Mode. This toggling between modes is initiated by the user pressing a designated button on one of the game control peripherals 32a, 32b or key on keypad 84.

The output 186 of the switch 182 is then fed to video overlay circuit 188. The video overlay circuit 188 is coupled to the video port 98 by the lines 114 of interface module 26. The video overlay circuit 188 receives digital data in a serial stream via one of the lines 114. The overlay circuit 188 places this data over the video signal which it receives from switch output 186. In this manner, the video image displayed on the television 30 will include the data written by video system computer 28 to video port 98. In the disclosed embodiment, the video overlay circuit 188 is a Model BU 2801S from Rohm Electronics, Antioch, Tenn., USA. The video overlay circuit 188 is remote from the video port 98, and communication therebetween is by extended TTL data lines. The overlay circuit 188 could be built inside the housing of interface module 26, and in fact, the TTL signal may not be properly transmitted if the lines 114 extend too far.

The output of the video overlay circuit 188 is fed to both a first outlet cable 190 and an RF modulator 192. The RF modulator 192 converts the video output of the video overlay circuit 188 to a radio frequency signal. The output of the RF modulator 192 is fed to a second outlet cable 194. In this manner, where the television 30 cannot accept video signal, it is coupled to the second outlet cable 194 as shown in FIG. 8. In cases where the television 30 can accept a video signal (such as with "cable ready" TVs) the television 30 is coupled to the first outlet cable 190.

In accordance with another aspect of the invention, the video port 98 may include an additional data line for controlling the CATV tuner 44. In these cases, the CATV tuner 44 may be incorporated in the video interface 38 itself. In this manner, the video system computer 28 can write additional control bits to video port 98. These additional control bits enable the video system computer 28 to control the CATV tuner 44 in response to user input (either via the game control peripherals 32a, 32b or the keypad 84). Thus, a user while exercising in Graphic Overlay Mode could conveniently change CATV channels.

When operating in Graphic Overlay Mode, the video system computer 28 accepts exercise data (such as pedal rpm, total calorie consumption, and heart rate), and writes this data to the video port 98 for superimposing display on the television 30. Ideally, the data should be displayed near a bottom corner of the screen, so as not to obscure the television image. The data may be displayed continuously, periodically, or in response to the user's command (via one of the game control peripherals 32a, 32b, for example).

While in Graphic Overlay Mode, the video system computer 28 can also control load resistance in accordance with a predefined exercise program, such as typically resident on the exercise computer. Such programs include: (i) generating random values for load resistance; (ii) adjusting load resistance to maintain constant heart rate; (iii) adjusting load resistance to maintain constant step rate or maximum rpm; (iv) generating load resistance in accordance with an aerobic interval training regimen; and (v) any other exercise program.

Thus, the video system computer 28 calculates or selects current and future loads. These load values can be transmitted to the exercise machine 22 for display on the program profile display 86, or can be graphically depicted via the overlay circuit 188 on the television 30.

Data Storage

As discussed above, the interface module 26 includes the SRAM 96. During interactive exercise operation, the video system computer 28 can write exercise and other data to the SRAM 96. This data remains resident in the interface module 26, even when the memory cartridge 34 (or, for that matter, video system computer 28) is replaced.

This feature is particularly beneficial for users who track historical exercise data. For example, there are fitness programs (or "personal trainers") which base workout intensity on past exercise performance. Such programs typically contemplate that the user will exercise with the same trainer program. Thus, when the trainer program is placed on a removable cartridge, the historical exercise data is stored on that cartridge. This in effect limits the user to that particular cartridge. If the user were to exercise with other cartridges, such as, for example, video game cartridges in accordance with the invention, then the historical data would not be properly accumulated.

This limitation is overcome by storing historical exercise data in the interface module SRAM 96. In this manner, the user is not tied to a single memory cartridge. For example, the user can play a number of different video games while still recording and preserving his exercise data. Also, the user can change cartridges during an exercise session without losing data.

Remote Control of Exercise Machine

Many of the more sophisticated exercise machines are computer controlled. For example, load and, particularly, the variation of load in accordance with a program, is controlled by a computer generated signal according to a preset exercise program or protocol. The computation and display of calorie consumption is performed by a computer. Computation of fitness levels and detection of heart rates are performed by the computer. Thus, many exercise machines include one or more microcomputers or micro controllers, along with a display and keypad for communication between the user and the computer.

These components significantly add to the cost of exercise machines. Cost is an important factor in the marketing of exercise machines, particularly exercise machines intended for home use. However, most people have in their home a television, and many have computer-based video systems, such as the Nintendo brand entertainment system. Thus the cost of computer-controlled exercise equipment can be reduced by eliminating the computer and display components from the equipment by substituting the processing and display power of a typical home television and video system to perform the exercise machine control and display functions.

Figure 9:
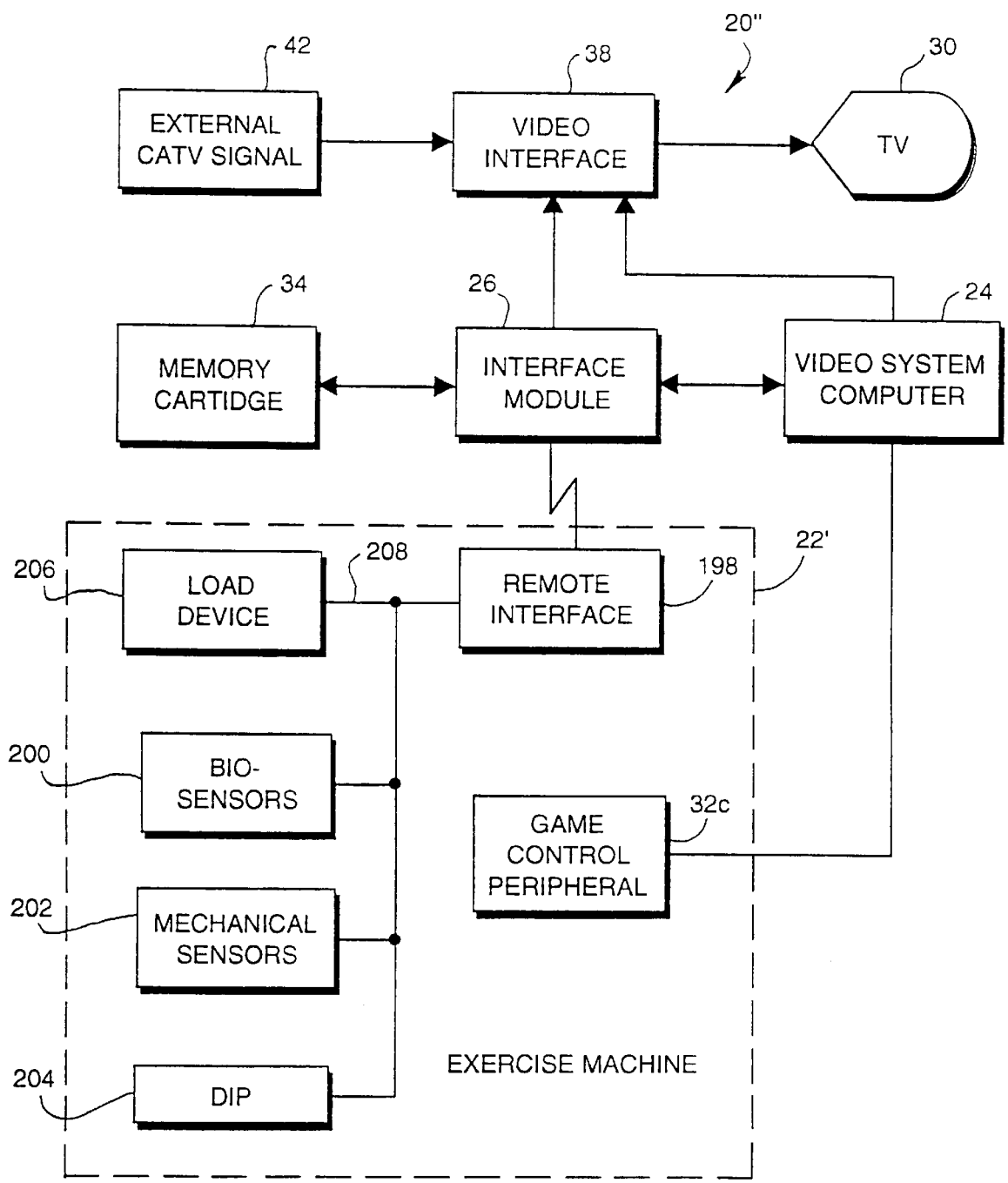
FIG. 9 is block diagram of a system in accordance with an alternative embodiment of the invention.

In accordance with this invention, an alternative embodiment 20' of the exercise video system 20 is illustrated in FIG. 9. This embodiment is similar to the system 20 except that it does not have a control and display panel such as panel 74 or a computer such as exercise computer 68. A remote interface 198 sends and receives serial RS-232 communications in accordance with a predetermined protocol. The video system computer 28 periodically, such as, for example, every 100 milliseconds sends a command byte. In response, the exercise machine remote interface 198 transmits a status packet of three bytes. The first byte is the output of a biosensor 200, the second byte is the output of a mechanical sensor 202 and the third byte is the output of a DIP switch 204. The setting of the DIP switch 204 indicates the type of exercise machine, and corresponds to the machine type byte $D_5$ of the status data packet 138 discussed above.

The exercise machine 22' is equipped with a load device 206, preferably an alternator with suitable control circuitry, which is responsive to a load control signal 208. In practice, the command byte received from the video system computer 28 is interpreted by the exercise machine 22' as the new value of the load control signal 208. The remote interface 198 includes a three-bit counter and a clock (not shown). The counter is coupled to the clock, and increments with each clock cycle. As the counter increments, it successively enables each of the load device 206, bio-sensor 200, mechanical sensor 202 and DIP switch 204. A latch included in the remote interface 198 is coupled to each of these devices, and holds data bytes received from and transmitted to the video system computer 28. When a command byte is received from the video system computer 28, the counter is reset to binary "000", which enables the load device 206 to read the byte in the data latch. The clock operating at a clock speed of about 200 Hz begins to increment the counter. When the counter is incremented to binary "001", it enables the biosensor 200 to write its contents to the latch. On the next clock pulse, the contents of the latch are transmitted to the video system computer 28, and the counter is incremented to binary "010", enabling the mechanical sensor 202 to write its contents to the latch. On the next clock pulse, the contents of the latch are transmitted to the video system computer 28, and the counter is incremented to binary "011", enabling the mechanical DIP switch 204 to write its contents to the latch. On the next clock pulse, the contents of the latch are transmitted to the video system computer 28, and the counter is incremented to binary "100". When the state of the counter is binary "100", the clock is disabled and the remote interface 198 is placed into a receive mode so that no further data is transmitted until the next command byte is received from the video computer 68. When the next command byte is received, the counter is reset to "000", and the above-described process is repeated.

In accordance with this embodiment, the video system computer 28 reads the values of the biosensor 200, mechanical sensor 202 and DIP switch 204, and computes elapsed time, calorie consumption and rate of calorie consumption. The video system computer 28 also determines the current and upcoming load resistance values, and displays all of this information on the television 30. This can be done in connection with a video game or other exercise programs. The video system computer 28 can also accept user input such as weight, exercise level and target heart rate using the game controllers 32a and 32b. To this end, prompts directing the user to enter the required data are displayed on the television 30.

Video Game Exercise Protocols

To maximize physical fitness and in particular, cardiovascular fitness, it is considered desirable to perform exercise according to predetermined exercise protocols. Many existing computerized aerobic-type exercise machines are programmed such that the user is led through a preset exercise program. For example, there are exercise bicycles that vary resistance levels and step machines that vary step rate in order to create an interval training program resulting in specific cardiovascular objectives. Similarly, such exercise machines are often programmed with protocols designed to provide aerobic workouts that will burn off a predetermined number of calories; last a specific period of time or maintain a designated heart rate. In one embodiment of the invention, the fitness results of the video games implemented in the system of FIG. 1 are improved by embedding exercise protocols in the game scenarios programmed in the cartridge 34.

An illustration of a video game containing an exercise protocol is provided in FIG. 14. In the lower portion of FIG. 14, resistance levels generated by the exercise machine 22 over a time period are indicated by a line 300. This resistance program is designed to produce an interval type workout having a duration of 12 minutes. In the upper portions of FIG. 14 are a series of representative video screens 302–308 displayed on the television 30 which are created by a video game program contained in the cartridge 34. Correspondence between the screens 302–308 and the resistance levels 300 is indicated by a set of dashed lines 310–316. The particular game illustrated in FIG. 14 is a bicycle road race where a road 318a–318d and associated terrain 320a–320b is projected forward from the user who, for the purpose of the game, is riding a bicycle 322. Steering of the bicycle on the road 318a–318d can be simulated by using the game controller 32c in the same manner that steering is simulated in standard video road race type games. The apparent speed of the user's bicycle can be changed by the user varying the rate that he is pedaling the exercise bicycle 22. The video game can also create other bicycle riders (not shown) to provide competition for the user.

To provide realism and visual feedback, when the resistance level is increased from a base level, for example, during a warm-up period 323 to a plateau resistance level 324, the video game will generate a screen such as the screens 318b and 318c that visually suggests to the user that riding the bicycle will require a greater effort. One method of accomplishing this effect is to move a horizon line 326a in the screen 302 from a base level upwardly to a position 326b in screen 304 so as to give the user the visual impression that he is riding up hill. This effect can also be accomplished by simulating sand, water or snow on the road 318c as shown on the screen 306 by a dotted portion 328 of the image. Using different visual effects to indicate increased riding effort is desirable when there is a relatively long period of increase resistance as in the case of the plateau portion 324 of the program 300. Here, as depicted on screen 306, the sand 328 is used to suggest increased riding effort after the first portion of the plateau 324 is represented by the hill in the screen 304. A variety of other methods of displaying increased riding effort situations can be used including placing obstacles in the road 318a–318b; depicting the bicycle 322 as having a flat tire; or having an opposition rider knock the user off the bicycle 322 so that the user is required to start riding again with the increased effort normally associated with starting off on a bicycle. By the same token, when the resistance program 300 results in a decrease in user resistance, as shown for instance at a point 330 in the program 300, the apparent horizon 326d in the screen 308 can be moved downwardly. This will provide the user with the visual impression that he is riding down hill.

In addition, in some circumstances, it can be desirable to display upcoming hills. In the screen 308, for example, the road 318d is shown traversing a pair of upcoming hills 332 and 334. By showing upcoming hills, the user can be prepared for increased effort levels. Also, the upcoming hills can simultaneously be displayed on the LED display 86 of the exercise bicycle panel 74.

One problem that can occur when an exercise protocol is imbedded in a video game is that the user's rate of exercise can affect the operation of the video game so that the game display may not match the programmed exercise routine. For example, in the game illustrated in FIG. 14, if the user pedals the exercise cycle 322 at a rate greater than the nominal rate of 80 RPM for this machine, the bike 322 will move more quickly along the road 318a–318d toward the hills displayed on the screens 302–308. Thus, the hills or displayed resistances shown in screens 304 or 306 will appear on the display 30 before the programmed resistance levels 300 are applied to the exercise bicycle 322. Likewise, if the exercise bicycle is pedaled at a slower rate, the programmed resistance 300 would occur before a hill or other images suggesting increased effort is generated on the display 30.

It is, therefore, desirable to supply the video game program based on an exercise protocol with logic that will compensate for the user's actual rate of exercise. In the video game illustrated in FIG. 14, for example, the distances to the hills projected on the screens 302–308 can be programmed to be a function of the time when the next programmed resistance level 300 is to occur and the rate at which the exercise bicycle 322 is pedaled. The following relation can be used by the video game program in the cartridge 34 to define the apparent distance $d_n$ as:

$$d_n = K(t_n - t_c) \frac{V_K}{V_c}$$

where:

$t_n$ is the time programmed for the next resistance level according to the exercise protocol.

$t_c$ is the current time.

$V_k$ is the nominal speed of exercise for the exercise machine.

$V_c$ is the actual speed of exercise.

K is a scaling constant.

By using the above relation, the video game program can continue to calculate the distance to the next hill or other displayed source of increased riding effort and generate the appropriate screens for display on the television 30.

Similar formulations can be used to adjust a video game display where the exercise protocol is based on distance, calories burned or heart rate and where the user can vary exercise machine operating parameters such as pedal or step rate or resistance.

It should be noted that the video game with the exercise protocol described above in connection with FIG. 14 can be termed an open loop system. In this approach, the video game is designed to lead the user through a preset exercise routine. However, the general approach described above can be used to provide video game exercise systems with video games that operate in a closed loop manner. For example, the exercise machine 22 can be used to monitor heart rate as described in connection with FIG. 4 and the video game can be programmed to maintain the user's heart rate at a prescribed level. This can be done, for instance, by varying the resistance of the exercise machine 22 and generating corresponding screen displays of the type shown in FIG. 14.

We claim:

1. A video exercise system comprising:

a physical exercise apparatus having physical resistance means for generating a user resistance force;

a video display, a game control peripheral operable by the user; and control means operatively connected to said exercise apparatus, said game control peripheral and said video display for generating a user interactive game on said video display wherein said interactive game includes a game scenario having a predetermined aerobic exercise protocol in order to achieve a predetermined aerobic workout objective wherein said user resistance is varied in accordance with said predetermined aerobic exercise protocol.

2. The system of claim 1 wherein said aerobic exercise protocol includes a predetermined set of said user resistances for predetermined times.

3. The system of claim 2 wherein said control means includes speed means for controlling said game so as to compensate for the user's rate of exercise.

4. The system of claim 1 wherein said predetermined aerobic workout objective is to burn off a predetermined number of calories.

5. The system of claim 1 wherein said predetermined aerobic workout objective is to maintain a predetermined heart rate.

6. The system of claim 1 wherein said predetermined aerobic protocol includes an aerobic workout having a predetermined duration of time.

7. The system of claim 1 wherein said predetermined aerobic protocol includes an interval workout.

8. The system of claim 1 wherein said control means includes speed means, responsive to the user's rate of exercise, for graphically displaying on said video display an upcoming change in said user resistance according to said aerobic exercise protocol and the user's rate of exercise.

9. The system of claim 8 wherein said graphical display of an upcoming change is represented as on obstacle at a predetermined distance from a reference point and said predetermined distance increases a function of the user's rate of exercise.

10. The system of claim 9 wherein said predetermined distance from said reference point is computed as a function of the relation: $d_n = K(t_n - t_c) V_K/V_C$ where $d_n$ is the predetermined distance from said reference point, $t_n$ is a time programmed for the next resistance level according to said aerobic exercise protocol, $t_c$ is the current time, $V_K$ is a nominal speed of exercise for said exercise apparatus, $V_C$ is the actual speed of said exercise apparatus and K is a scaling constant.

* * * * *